United States Patent
Liu

(10) Patent No.: US 12,390,615 B2
(45) Date of Patent: Aug. 19, 2025

(54) SYSTEMS AND METHODS FOR CONTROLLING HUMIDITY OUTPUT IN A HUMIDIFIER

(71) Applicant: Fisher & Paykel Healthcare Limited, Auckland (NZ)

(72) Inventor: Po-Yen Liu, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 835 days.

(21) Appl. No.: 17/437,376

(22) PCT Filed: Mar. 11, 2020

(86) PCT No.: PCT/NZ2020/050024
§ 371 (c)(1),
(2) Date: Sep. 8, 2021

(87) PCT Pub. No.: WO2020/185100
PCT Pub. Date: Sep. 17, 2020

(65) Prior Publication Data
US 2022/0296846 A1    Sep. 22, 2022

Related U.S. Application Data

(60) Provisional application No. 62/816,623, filed on Mar. 11, 2019.

(51) Int. Cl.
*A61M 16/16* (2006.01)
*A61M 16/00* (2006.01)
*A61M 16/10* (2006.01)

(52) U.S. Cl.
CPC ........ *A61M 16/162* (2013.01); *A61M 16/024* (2017.08); *A61M 16/109* (2014.02);
(Continued)

(58) Field of Classification Search
CPC .................................................. A61M 16/1045
See application file for complete search history.

(56) References Cited

U.S. PATENT DOCUMENTS

2009/0065002 A1* 3/2009 Hunt ................. A61M 16/1085
128/203.17
2011/0120462 A1* 5/2011 Tatkov .............. A61M 16/0465
128/203.14

(Continued)

FOREIGN PATENT DOCUMENTS

JP     2005-537083     12/2005
JP     2011-521705      7/2011
(Continued)

OTHER PUBLICATIONS

International Search Report and Written Opinion issued in PCT Application No. PCT/NZ2020/050024, mailed Jun. 17, 2020, in 22 pages.

*Primary Examiner* — Joseph D. Boecker
*Assistant Examiner* — Thomas W Greig
(74) *Attorney, Agent, or Firm* — Knobbe Martens Olson & Bear LLP

(57) ABSTRACT

A respiratory assistance system can include a humidifier used for delivery of heated and humidified gases to a patient includes a humidification chamber with an inlet and associated sensor, an associated heater and sensor, an inspiratory conduit with an associated heater and sensor, and an unheated patient interface, such as a face mask. A humidifier can include a control system configured to change a humidification chamber outlet temperature set point or an amount of generated humidity, including for example, a maximum outlet temperature set point, as a function of inlet gas temperature. The control system can reduce and/or minimize
(Continued)

rainout (i.e. condensate) while maintaining a substantially consistent humidity in the gases delivered to a patient.

18 Claims, 18 Drawing Sheets

(52) U.S. Cl.
CPC ............... *A61M 2205/3368* (2013.01); *A61M 2205/3653* (2013.01)

(56) References Cited

U.S. PATENT DOCUMENTS

| | | |
|---|---|---|
| 2012/0167880 A1 | 7/2012 | Jacob |
| 2014/0166005 A1 | 6/2014 | Tatkov et al. |
| 2015/0020801 A1* | 1/2015 | Frame .................. G16H 40/63 128/202.22 |
| 2018/0250490 A1* | 9/2018 | Burgess ................ A61M 16/16 |

FOREIGN PATENT DOCUMENTS

| | | | |
|---|---|---|---|
| JP | 2019-505297 | 2/2019 | |
| WO | WO 2004/020031 | 3/2004 | |
| WO | WO 2006/019323 | 2/2006 | |
| WO | WO 2015/135040 | 9/2015 | |
| WO | WO 2015/167347 | 11/2015 | |
| WO | WO-2016080847 A1 * | 5/2016 | ........ A61M 16/0003 |
| WO | WO 2017/126980 | 7/2017 | |

* cited by examiner

SYSTEMS AND METHODS FOR CONTROLLING HUMIDITY OUTPUT IN A HUMIDIFIER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

The present disclosure generally relates to humidifying gases for medical procedures, for example, respiratory humidification, humidification during high flow therapy and humidification during anaesthesia/sedation, or other medical procedures in which humidified gases are provided to a patient. More particularly, the present disclosure relates to a respiratory assistance system comprising at least a humidifier and a method for operation of a humidifier that controls the temperature and/or humidity levels of respiratory gases.

BACKGROUND

During unassisted inspiration, the upper airway heats and humidifies inspired gases to a humidity condition of 100% relative humidity at a body temperature of about 37° C., or about 44 mg/L absolute humidity. It can be beneficial for a humidifier, operating as part of a respiratory assistance system, to heat and humidify the respiratory gases to a humidity condition such that the respiratory gases reaching the patient's lungs are humidified, so as to reduce any adverse physiological effects due to dry gases being provided to the patient's airways.

SUMMARY

Many humidifiers can monitor the amount of humidity added to the incoming gases, for example, by controlling power to a heater plate of the humidifier to control the absolute humidity of the gases being humidified. Some humidifiers, however, do not always have an integrated hygrometer or otherwise to obtain information about an incoming gas or gases, which makes it more difficult to directly detect humidity of the incoming gas or gases. Humidifiers are often used with dry gases sources e.g. a canister or wall gases source or ventilators that provide dry gases (i.e. unhumidified gases). When humidifiers are connected to room air entraining ventilators as the gases source, the lack of ability to directly detect incoming humidity can cause inaccuracies in the delivered humidity, which may lead to an undesirable amount of condensation formation (also known as the "rain out") in an inspiratory tube (i.e. a gases delivery conduit) or patient interface, often due to over-humidification of the gases.

This undesirable amount of condensation (i.e. rain out) can be due to the air entrained by room air entraining ventilators typically having a higher humidity than dry gas from a wall source or canister. The difference in humidity in room air and gas from a wall source or canister can be more prominent in more tropical countries and regions. Additionally, a room air entraining ventilator commonly uses a turbine, which may heat up the gas.

The increased humidity in the incoming air can in turn result in excess humidity being delivered to a patient because most humidifiers heat and humidify the incoming gas under the assumption that the incoming gas is dry. Such a humidifier may add too much humidity to the incoming room air in an effort to reach a predetermined humidification chamber outlet set point under the assumption of a dry incoming gas.

Operating under the above assumption, the existing humidity from the room air present can cause the dew point of the gases in the gas flow path to be higher than when dry gas is used as a gas source to the humidifier. Thus, when room air is used as the gas source, the humidity of the chamber outlet gases is typically higher. When the humidity of the chamber outlet gases is higher, the temperature of the gases has to be maintained at or above the dew point in order prevent condensation. Comparatively, when dry gases are used as the gas source, the chamber outlet gases have may have less humidity and the dew point of the gases may be lower. Thus, the temperature of the gases where dry gas is used as the gas source can be lower due to a lower dew point. As the gases flow cools along the flow path between the humidification chamber and the patient interface, this higher than anticipated humidity of the gases from the room entraining ventilator, results in a decrease in the available range of temperature that the gases are able to cool down by before reaching the dew point and resulting in rain out. Rain out is particularly a problem at the patient interface, which is at the distal or patient end of the inspiratory tube (i.e. delivery tube), resulting in discomfort and/or inconvenience to the patient. Further, the problems of rain out are amplified because the patient interface and components of the patient interface are unheated, which results in a more rapid temperature drop as compared to the inspiratory tube that is normally heated. Further, condensation within the tube or patient interface can be a risk to a patient.

The present disclosure provides systems and methods for reducing rain out in the inspiratory tube and/or the patient interface while still delivering a substantially consistent target humidity to the patient. The present disclosure relates to systems and methods that reduce rain out while humidifying ambient air and while still providing a minimum therapeutic humidity to the patient. The minimum therapeutic humidity reduces drying or desiccation of the airways of the patient and improves patient comfort.

The humidifier may provide different levels of therapeutic humidity for different therapy applications, such as in a hospital or homecare environment. For example, the humidifier can deliver a desired humidity level of about 44 mg/L BTPS (about 37° C. fully saturated) for invasive and/or high flow therapies and/or about 32 mg/L BTPS (about 31° C. fully saturated) for non-invasive therapies. Other suitable patient comfort settings could also be delivered for various therapy types.

The present system can output a desired humidity level in gases delivered to a patient across a range of inlet source conditions, such as different chamber inlet temperatures (i.e. inlet temperatures) and/or gaseous sources, including room air entraining ventilators. Advantageously, the system can reduce rainout by, for example, reducing the humidity output of the humidification chamber below a desired humidity.

In some examples, a desired humidity of gases delivered to a patient by a humidifier may be based on one or more assumptions about the incoming gases, such as that incoming gases are dry. However, these assumptions are not always correct. For example, when incoming gases, such as ambient air, contain an amount of humidity, humidity of gases delivered to a patient may be too high, causing rainout. In some systems, rainout may be managed through the use of a humidity sensor or other direct measurement of the humidity of the incoming gases. However, the present system can reduce the humidity output of the humidification chamber of a humidifier while maintaining a substantially consistent humidity in the gases delivered to a patient without the use of a humidity sensor and/or receiving direct input of the incoming gas humidity. For example, the system can determine a parameter of the input gases and use the determined parameter as an indicator of the type of gases being input and/or the type of gases source.

Example systems and methods for reducing excess condensation in a humidifier while still delivering a substantially consistent humidity of gases delivered to the patient, regardless of gases source type (for example, regardless of ventilator type), are described herein. Certain aspects, advantages, and novel features of the present disclosure are described herein. It is to be understood that not necessarily all such advantages may be achieved in accordance with any particular embodiment of the present disclosure. Thus, the features, aspects, and advantages of the present disclosure may be embodied or carried out in a manner that achieves or selects one advantage or group of advantages as taught herein without necessarily achieving other advantages as may be taught or suggested herein.

A humidifier for humidifying a gases flow provided to a user can include: a base unit can include a heater plate; a humidification chamber may be configured to retain a humidification fluid, the humidification chamber can include: a conductive base, one or more wall portions may be configured to couple to the base portion, an inlet, and an outlet; at least one inlet temperature sensor located within or adjacent the inlet of the humidification chamber; at least one outlet temperature sensor located within or adjacent the outlet of the humidification chamber; and a controller may be configured to: output a heater plate control signal to control an amount of power provided to the heater plate in response to an outlet temperature measured from signals received from the outlet temperature sensor; determine an inlet temperature of gases being received into the humidification chamber based on signals received from the inlet temperature sensor; determine that the inlet temperature exceeds a threshold temperature; and reduce a target humidity of gases leaving the outlet of the humidification chamber in response to the inlet temperature exceeding the threshold temperature.

The humidifier may reduce a target humidity, the controller may be configured to reduce the amount of power provided to the heater plate in response to the inlet temperature exceeding the threshold temperature. The reduced target humidity is achieved by controlling the power provided to the heater plate. The amount of power provided to the heater plate generates a requisite target humidity. The target humidity is reduced from a target humidity limit to a lower target humidity. In another example implementation the controller is configured to cap or limit the target humidity to a second humidity if the inlet temperature exceeds a threshold temperature.

The controller may be configured to reduce the amount of power to less than or equal to a power threshold.

The power threshold may be set so as to achieve a minimum dew point of 19° C.

The power threshold may be set so as to achieve a minimum humidity output of 15 mg/L.

The power threshold may be set so as to achieve a dew point of 25° C.

The power threshold may be set so as to achieve a humidity output of 22 mg/L.

The controller may be configured to control the amount of power provided to the heater plate according to a first mode when the inlet temperature is below the threshold temperature and a second mode when the inlet temperature exceeds the threshold temperature.

In a first mode the controller may be configured to set a power set point or chamber outlet set point or a heater plate temperature set point to achieve a minimum humidity of at least 15 mg/L. In a second mode the controller may be configured to set a power set point or chamber outlet set point or a heater plate temperature set point to achieve a minimum humidity of at least 22 mg/L.

In a first mode the controller may be configured to set a power set point or chamber outlet set point or a heater plate temperature set point to achieve a minimum dew point of at least 19° C. In a second mode the controller may be configured to set a power set point or chamber outlet set point or a heater plate temperature set point to achieve a minimum dew point of at least 25° C.

The controller may be configured to control the amount of power provided to the heater plate power as per a first function, the first function being applied when the inlet temperature may be below the threshold temperature.

The controller may be configured to control the amount of power provided to the heater plate power as per a second function that may be different than the first function, the second function being applied when the inlet temperature exceeds the threshold temperature. The first and second functions can together define a piecewise function.

The controller may be configured to reduce a target outlet temperature if the inlet temperature exceeds a threshold temperature. The target outlet temperature is reduced from a target outlet temperature limit to a lower target outlet temperature if the inlet temperature exceeds a threshold temperature. In another example the controller is configured to restrict or cap the target outlet temperature.

The controller may be configured to reduce a target heater plate temperature if the inlet temperature exceeds a threshold temperature. The target heater plate temperature is reduced from a target heater plate temperature limit to a lower target heater plate temperature if the inlet temperature exceeds a threshold temperature. In another example the controller is configured to restrict or cap the target heater plate temperature.

The threshold temperature may be between 22° C. and 24° C.

The threshold temperature may be 22° C.

The threshold temperature may be 24° C.

The threshold temperature may vary according an outlet temperature set point.

A desired dew point may be selected by a user.

The humidifier may be operable in one of a plurality of modes, each mode defining a plurality of desired dew points, the controller may be configured to reduce the amount of humidity generated based on the inlet temperature exceeding the threshold, when operating in any one of the plurality of modes.

The plurality of modes can include an invasive mode, a non-invasive mode and a high flow mode.

A mode may be manually selectable by a user.

The non-invasive mode can include desired dew points of 31° C., 29° C., 27° C., and 25° C.

The humidifier may be operable in one of a plurality of modes, each mode defining a plurality of outlet temperature set points, the controller may be configured to reduce the amount of humidity generated based on the inlet temperature exceeding the threshold, when operating in any one of the plurality of modes.

The target humidity for an outlet temperature set point may be predefined when the inlet temperature may be below the threshold temperature and an amount of humidity generated for that outlet temperature set point may be reduced to a lower predefined value if the inlet temperature exceeds a threshold.

A humidifier for humidifying a gases flow provided to a user can include: a base unit can include a heater plate; a humidification chamber may be configured to retain a humidification fluid, the humidification chamber can include: a conductive base, one or more wall portions may be configured to couple to the base portion, an inlet, and an outlet; at least one inlet temperature sensor located within or adjacent the inlet of the humidification chamber; at least one outlet temperature sensor located within or adjacent the outlet of the humidification chamber; and an electronic controller may be configured to: output a heater plate control signal to control an amount of power provided to the heater plate in response to an outlet temperature measured from signals received from the outlet temperature sensor; determine an inlet temperature of gases being received into the humidification chamber based on signals received from the inlet temperature sensor; determine if the inlet temperature exceeds a threshold temperature; and reduce a target humidity of gases leaving the outlet of the humidification chamber in response to the inlet temperature exceeding the threshold temperature.

The humidifier may reduce a target humidity, the controller may be configured to reduce the amount of power provided to the heater plate in response to the inlet temperature exceeding the threshold temperature.

The controller may be configured to reduce the amount of power to less than or equal to a power threshold.

The reduced amount of power below a power threshold delivered to the heater plate reduces the humidity output of the humidifier. The controller is configured to deliver power to the heater plate that corresponds to the target humidity. The humidifier outputs the target humidity or almost the target humidity due to power supplied to the heater plate of the humidifier.

The power threshold may be set so as to achieve a minimum dew point of 19° C.

The power threshold may be set so as to achieve a minimum humidity output of 15 mg/L.

The power threshold may be set so as to achieve a dew point of 25° C.

The power threshold may be set so as to achieve a humidity output of 22 mg/L.

The controller may be configured to control the amount of power provided to the heater plate according to a first mode when the inlet temperature is below the threshold temperature and a second mode when the inlet temperature exceeds the threshold temperature.

In a first mode the controller may be configured to set a power set point or chamber outlet set point or a heater plate temperature set point to achieve a minimum humidity of at least 15 mg/L. In a second mode the controller may be configured to set a power set point or chamber outlet set point or a heater plate temperature set point to achieve a minimum humidity of at least 22 mg/L.

In a first mode the controller may be configured to set a power set point or chamber outlet set point or a heater plate temperature set point to achieve a minimum dew point of at least 19° C. In a second mode the controller may be configured to set a power set point or chamber outlet set point or a heater plate temperature set point to achieve a minimum dew point of at least 25° C.

The controller may be configured to control the amount of power provided to the heater plate power as per a first function, the first function being applied when the inlet temperature may be below the threshold temperature.

The controller may be configured to control the amount of power provided to the heater plate power as per a second function that may be different than the first function, the second function being applied when the inlet temperature exceeds the threshold temperature.

The first function and the second function define a piecewise function. The piecewise function may define the heater plate power. A further piecewise function may define a target humidity. The target humidity piecewise function may correspond to or relate to the piecewise function defining the heater plate power.

The controller may be configured to reduce a target outlet temperature if the inlet temperature exceeds a threshold temperature.

The controller may be configured to reduce a target heater plate temperature if the inlet temperature exceeds a threshold temperature.

The threshold temperature may be between 22° C. and 24° C.

The threshold temperature may be 22° C.
The threshold temperature may be 24° C.
The threshold temperature may vary according to an outlet temperature set point.

A desired dew point may be selected by a user.

The humidifier may be operable in one of a plurality of modes, each mode defining a plurality of desired dew points, the controller may be configured to reduce the amount of humidity generated based on the inlet temperature exceeding the threshold, when operating in any one of the plurality of modes.

The plurality of modes can include an invasive mode, a non-invasive mode and a high flow mode.

A mode may be manually selectable by a user.

The non-invasive mode can include desired dew points of 31° C., 29° C., 27° C., and 25° C.

The humidifier may be operable in one of a plurality of modes, each mode defining a plurality of outlet temperature set points, the controller may be configured to reduce the amount of humidity generated based on the inlet temperature exceeding the threshold, when operating in any one of the plurality of modes.

The target humidity for an outlet temperature set point may be predefined when the inlet temperature may be below the threshold temperature and an amount of humidity generated for that outlet temperature set point may be reduced to a lower predefined value if the inlet temperature exceeds a threshold.

A humidifier for humidifying a gases flow provided to a user can include: a base unit including a heater plate; a removable humidification chamber can include a conductive base and one or more walls extending from the conductive base, wherein the one or more walls and the conductive base defines a chamber space to retain a humidification fluid, the humidification chamber further can include an inlet and an outlet; at least one inlet temperature sensor located within or adjacent the inlet of the humidification chamber; at least one outlet temperature sensor located within or adjacent the outlet of the humidification chamber; and an electronic controller that may be configured to: output a heater plate control signal to control an amount of power provided to the heater plate in response to an outlet temperature measured from signals received from the outlet temperature sensor; measure an inlet temperature of gases being received into the humidification chamber based on signals received from the inlet temperature sensor; determine that the inlet temperature exceeds a threshold temperature; and set a first outlet temperature set point if the inlet temperature is less than the threshold temperature and set a second outlet temperature set point if the inlet temperature of the gases exceeds or is equal to the threshold temperature.

The threshold temperature may be between 22° C. and 24° C.

The first outlet temperature set point may be between 24° C. to 32° C.

The second outlet temperature set point may be between 19° C. to 27° C.

The electronic controller may be configured to control power provided to the heater plate based on the chamber outlet temperature set point.

The electronic controller may be configured to reduce the heater plate power when the inlet temperature exceeds the threshold temperature.

The electronic controller is configured to control power delivery such that a first power is delivered to the heater plate when the inlet temperature is less than the threshold temperature and a second power is delivered to the heater plate if the inlet temperature exceeds or is equal to the threshold temperature.

The electronic controller is configured to cap or limit the amount of power delivered to the heater plate if the inlet temperature exceeds or is equal to the threshold temperature.

The electronic controller may be configured to set a first chamber outlet temperature set point that corresponds to a humidity value between 21 mg/L to 34 mg/L.

The electronic controller may be configured to set a second chamber outlet temperature set point that corresponds to a humidity value of between 14 mg/L to 25 mg/L.

The electronic controller may be configured to reduce the power supplied to the heater plate if the inlet temperature exceeds a temperature threshold.

The power supplied to the heater plate is reduced from a power limit. In another example the power supplied to the heater plate may be capped or limited if the inlet temperature exceeds a temperature threshold.

The electronic controller may be configured to provide a heater plate power corresponding to the first or second chamber outlet set point temperature such that a required amount of humidity may be generated.

A humidifier for humidifying a gases flow provided to a user can include: a base unit including a heater plate; a removable humidification chamber can include a conductive base and one or more walls extending from the conductive base, wherein the one or more walls and the conductive base defines a chamber space to retain a humidification fluid, the humidification chamber further can include an inlet and an outlet; at least one inlet temperature sensor located within or adjacent the inlet of the humidification chamber and configured to determine an inlet temperature; at least one outlet temperature sensor located within or adjacent the outlet of the humidification chamber and configured to determine an outlet temperature; and an electronic controller configured to: determine if an inlet temperature exceeds a threshold temperature; and cap a maximum allowable chamber outlet temperature, heater plate temperature, or allowable heater plate power for a corresponding inlet temperature.

The maximum allowable chamber outlet temperature as defined by the second function may be less than the maximum allowable chamber outlet temperature as defined by the first function.

The absolute humidity generated by the first function may be greater than the humidity output generated by the second function.

The humidifier can include a heater plate, wherein the controller may be configured to control power provided to the heater plate based on the maximum allowable outlet temperature.

The controller may be configured to control power provided to the heater plate based on the first function or the second function.

The controller may be configured to use the first function when the gases source may be a cold dry gases source.

The controller may be configured to use the second function when the gases source may be a room air entraining gases source.

A humidifier for humidifying a gases flow provided to a user can include: a base unit including a heater plate; a removable humidification chamber can include a conductive base and one or more walls extending from the conductive base, wherein the one or more walls and the conductive base defines a chamber space to retain a humidification fluid, the humidification chamber further can include an inlet and an outlet; at least one inlet temperature sensor located within or adjacent the inlet of the humidification chamber and configured to measure an inlet temperature; at least one outlet temperature sensor located within or adjacent the outlet of the humidification chamber and configured to measure an outlet temperature; and an electronic controller configured to: control to a predefined maximum allowable outlet temperature for a corresponding inlet temperature, wherein the maximum allowable outlet temperature may be related to the inlet temperature defined by a first function; and based on the inlet temperature, apply a second function defining new maximum allowable outlet temperatures for corresponding inlet temperatures.

The maximum allowable chamber outlet temperatures as defined by the second function may be less than the maximum allowable chamber outlet temperature as defined by the first function.

The absolute humidity generated by the first function may be greater than the humidity output generated by the second function.

The humidifier can include a heater plate, wherein the controller may be configured to control power provided to the heater plate based on the maximum allowable outlet temperature.

The controller may be configured to control power provided to the heater plate based on the first function or the second function.

The controller may be configured to use the first function when the gases source may be a cold dry gases source.

The controller may be configured to use the second function when the gases source may be a room air entraining gases source.

The controller is configured to use or implement the first function if the inlet temperature is less than a threshold temperature and the controller is further configured to use or implement the second function if the inlet temperature is greater than or equal to the threshold temperature.

An electronic controller for controlling humidity in a gases flow provided to a user using a humidifier can include a heater plate in a base unit and a humidification chamber including a conductive base and one or more walls extending from the conductive base, the humidification chamber further can include an inlet and an outlet, the humidification chamber configured to retain a humidification fluid, the controller may be configured to: output a heater plate control signal to control an amount of power provided to a heater plate of the humidifier in response to an outlet temperature of the humidification chamber measured from signals received from an outlet temperature sensor; measure an inlet temperature of gases being received into the humidification chamber based on signals received from an inlet temperature sensor; determine that the inlet temperature exceeds a threshold temperature; and reduce a target humidity of gases leaving the outlet of the humidification chamber in response to the inlet temperature exceeding the threshold temperature.

To reduce the target humidity, the controller may be configured to reduce the amount of power provided to the heater plate in response to the inlet temperature exceeding the threshold temperature.

The controller may be configured to reduce the amount of power to less than or equal to a power threshold.

The power threshold may be set so as to achieve a minimum dew point of 19° C.

The power threshold may be set so as to achieve a minimum humidity output of 15 mg/L.

The power threshold may be set so as to achieve a dew point of 25° C.

The power threshold may be set so as to achieve a humidity output of 22 mg/L.

The electronic controller may be configured to control the amount of power provided to the heater plate according to a first mode when the inlet temperature may be below the threshold temperature and a second mode when the inlet temperature exceeds the threshold temperature.

In a first mode the controller may be configured to set a power set point or chamber outlet set point or a heater plate temperature set point to achieve a minimum humidity of at least 15 mg/L. In a second mode the controller may be configured to set a power set point or chamber outlet set point or a heater plate temperature set point to achieve a minimum humidity of at least 22 mg/L.

In a first mode the controller may be configured to set a power set point or chamber outlet set point or a heater plate temperature set point to achieve a minimum dew point of at least 19° C. In a second mode the controller may be configured to set a power set point or chamber outlet set point or a heater plate temperature set point to achieve a minimum dew point of at least 25° C.

The electronic controller may be configured to output the heater plate control signal as per a first function, the first function being applied when the inlet temperature may be below the threshold temperature.

The electronic controller may be configured to output the heater plate control signal according to a second function that may be different than the first function, the second function being applied when the inlet temperature exceeds the threshold temperature.

In one example the first and second functions define a piecewise function.

The electronic controller may be configured to reduce a target outlet temperature if the inlet temperature exceeds a threshold temperature.

The electronic controller may be configured to reduce a target heater plate temperature if the inlet temperature exceeds a threshold temperature.

The threshold temperature may be between 22° C. and 24° C.

The threshold temperature may be 22° C.

The threshold temperature may be 24° C.

The threshold temperature may vary according an desired dew point.

The desired dew point may be selected by a user.

The controller may be configured to: determine a humidifier mode of a plurality of modes, wherein a mode defines a plurality of desired dew points; and determine a temperature threshold based on the humidifier mode.

The plurality of modes can include an invasive mode, a non-invasive mode and a high flow mode.

A mode may be manually selectable by a user.

The non-invasive mode can include desired dew points of 31° C., 27° C., and 25° C.

The target humidity for an outlet temperature set point may be predefined when the inlet temperature may be below the threshold temperature and an amount of humidity generated for that outlet temperature set point may be reduced to a lower predefined value if the inlet temperature exceeds a threshold.

A method of reducing condensation in an outlet of a humidifier can include: receiving an inlet temperature of gases being received into a humidification chamber based on signals received from an inlet temperature sensor; determining that the inlet temperature exceeds a threshold temperature; and reducing a target humidity of gases leaving an outlet of the humidification chamber in response to the inlet temperature exceeding the threshold temperature.

Reducing a target humidity can include reducing the amount of power provided to the heater plate in response to the inlet temperature exceeding the threshold temperature. The amount of power provided to the heater plate is capped or bounded in response to the inlet temperature exceeding the threshold temperature.

Reducing the amount of power provided to the heater plate can include reducing the amount of power to less than or equal to a power threshold.

The power threshold may be set so as to achieve a minimum dew point of 19° C.

The power threshold may be set so as to achieve a minimum humidity output of 15 mg/L.

The power threshold may be set so as to achieve a dew point of 25° C.

The power threshold may be set so as to achieve a humidity output of 22 mg/L.

Reducing the amount of power can include controlling the amount of power provided to the heater plate according to a first mode when the inlet temperature may be below the threshold temperature and a second mode when the inlet temperature exceeds the threshold temperature.

In a first mode a power set point or chamber outlet set point or a heater plate temperature set point may be set to achieve a minimum humidity of at least 15 mg/L. In a second mode a power set point or chamber outlet set point or a heater plate temperature set point may be set to achieve a minimum humidity of at least 22 mg/L.

In a first mode a power set point or chamber outlet set point or a heater plate temperature set point may be set to achieve a minimum dew point of at least 19° C. In a second mode a power set point or chamber outlet set point or a heater plate temperature set point may be set to achieve a minimum dew point of at least 25° C.

Reducing the amount of power can include controlling the amount of power provided to the heater plate power as per a first function, the first function being applied when the inlet temperature may be below the threshold temperature.

Reducing the amount of power can include controlling the amount of power provided to the heater plate power as per a second function that may be different than the first function, the second function being applied when the inlet temperature exceeds the threshold temperature.

Reducing a target outlet temperature if the inlet temperature exceeds a threshold temperature Reducing a target heater plate temperature if the inlet temperature exceeds a threshold temperature.

The threshold temperature may be between 22° C. and 24° C.

The threshold temperature may be 22° C.

The threshold temperature may be 24° C.

The threshold temperature may vary according a desired dew point.

The desired dew point may be selected by a user.

The method may further include determining a humidifier mode of a plurality of modes, wherein a mode defines a plurality of desired dew points; and determining a temperature threshold based on the humidifier mode.

The plurality of modes can include an invasive mode, a non-invasive mode and a high flow mode.

The mode may be manually selectable by a user.

The non-invasive mode can include desired dew points of 31° C., 29° C., 27° C., and 25° C.

The target humidity for an outlet temperature set point may be predefined when the inlet temperature may be below the threshold temperature and an amount of humidity generated for that outlet temperature set point may be reduced to a lower predefined value if the inlet temperature exceeds a threshold.

A controller for operating a humidifier may be configured to: receive an inlet temperature of gases being received into a humidification chamber based on signals received from an inlet temperature sensor; determine that the inlet temperature exceeds a threshold temperature; and reduce a target heater plate power or target heater plate temperature of gases leaving an outlet of the humidification chamber in response to the inlet temperature exceeding the threshold temperature.

To reduce the amount of power provided to the heater plate, the controller may be configured to reduce the amount of power to less than or equal to a power threshold.

The power threshold may be set so as to achieve a minimum dew point of 19° C.

The power threshold may be set so as to achieve a minimum humidity output of 15 mg/L.

The power threshold may be set so as to achieve a dew point of 25° C.

The power threshold may be set so as to achieve a humidity output of 22 mg/L.

To reduce the amount of power, the controller may be configured to control the amount of power provided to the heater plate according to a first mode when the inlet temperature is below the threshold temperature and a second mode when the inlet temperature exceeds the threshold temperature.

In a first mode the controller may be configured to set a power set point or chamber outlet set point or a heater plate temperature set point to achieve a minimum humidity of at least 15 mg/L. In a second mode the controller may be configured to set a power set point or chamber outlet set point or a heater plate temperature set point to achieve a minimum humidity of at least 22 mg/L.

In a first mode the controller may be configured to set a power set point or chamber outlet set point or a heater plate temperature set point to achieve a minimum dew point of at least 19° C. In a second mode the controller may be configured to set a power set point or chamber outlet set point or a heater plate temperature set point to achieve a minimum dew point of at least 25° C.

To reduce the amount of power, the controller may be configured to control the amount of power provided to the heater plate power as per a first function, the first function being applied when the inlet temperature may be below the threshold temperature.

To reduce the amount of power, the controller may be configured to reduce control the amount of power provided to the heater plate power as per a second function that may be different than the first function, the second function being applied when the inlet temperature exceeds the threshold temperature.

The threshold temperature may be between 22° C. and 24° C.

The threshold temperature may be 22° C.

The threshold temperature may be 24° C.

The threshold temperature may vary according a desired dew point.

The desired dew point may be selected by a user.

The controller may be configured to: determine a humidifier mode of a plurality of modes, wherein a mode defines a plurality of desired dew points; and determine a temperature threshold based on the humidifier mode.

The plurality of modes can include an invasive mode, a non-invasive mode and a high flow mode.

The mode may be manually selectable by a user.

The non-invasive mode can include desired dew points of 31° C., 29° C., 27° C., and 25° C.

The target humidity for an outlet temperature set point may be predefined when the inlet temperature may be below the threshold temperature and an amount of humidity generated for that outlet temperature set point may be reduced to a lower predefined value if the inlet temperature exceeds a threshold.

In a further aspect there is disclosed a humidifier for humidifying a gases flow provided to a user, the humidifier comprising:

a base unit comprising a heater plate;

a humidification chamber configured to retain a humidification fluid, the humidification chamber comprising:
  a conductive base,
  one or more wall portions configured to couple to the base portion,
  an inlet, and
  an outlet;

at least one inlet temperature sensor located within or adjacent the inlet of the humidification chamber;

at least one outlet temperature sensor located within or adjacent the outlet of the humidification chamber; and an electronic controller configured to:
  output a heater plate control signal to control an amount of power provided to the heater plate based at least partly on a function of an outlet temperature measured from signals received from the outlet temperature sensor;
  determine an inlet temperature of gases being received into the humidification chamber based on signals received from the inlet temperature sensor;
  determine that the inlet temperature exceeds a threshold temperature; and
  reduce, in response to the inlet temperature exceeding the threshold temperature, a maximum target humidity of gases leaving the outlet of the humidification chamber. The controller is configured to calculate an amount of power provided to heater plate based as a function of the outlet temperature. The controller is configured to cap the maximum allowable heater plate power based on a maximum allowable chamber outlet temperature set point.

The terms conduit and tube are interchangeably used herein.

DETAILED DESCRIPTION

Overview

Figure 1:
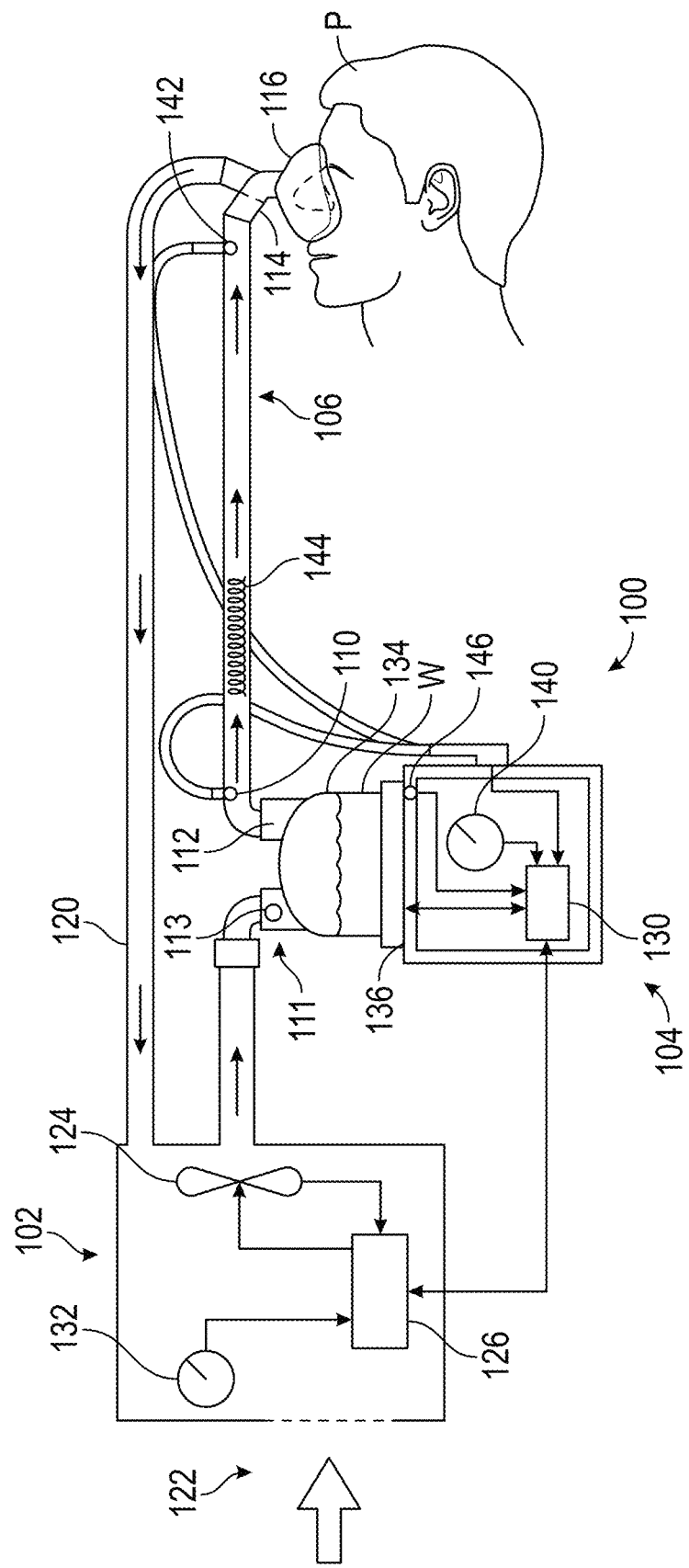
FIG. 1 illustrates a diagram of an example respiratory assistance system.

A respiratory assistance system for delivery of heated and humidified gases to a patient can include a patient interface configured to deliver a flow of respiratory gases received from a gases source, an inspiratory conduit configured to be in fluid communication with the patient interface and the gases source via a humidifier. The humidifier can include a humidification chamber having at least one wall that defines the chamber such that the chamber can hold a liquid, a chamber inlet, a chamber outlet, and a gases flow path between the chamber inlet and the chamber outlet. The chamber inlet can be configured to be in fluid communication with the gases source and the chamber outlet can be configured to be in fluid communication with the inspiratory conduit. The humidification chamber can hold a volume of liquid (for example, water). The humidifier can include a heater plate configured to heat the volume of liquid and the flow of respiratory gases in the gases flow path within the humidification chamber so as to heat and humidify the flow of respiratory gases. The humidifier can also include a controller having one or more hardware processors configured to control the amount of power delivered to the heater plate.

The humidifier examples disclosed herein can include a controller configured to change the humidification chamber outlet temperature set point as a function of chamber inlet temperature. For example, the controller can be configured to detect inlet gas temperature. As chamber inlet temperature increases, the controller can decrease the desired humidity level at the outlet to a lower level (such as a lower therapeutic level), allowing and accounting for additional humidity that may be added in the case of a room air entraining ventilator being the gas source that is connected to the humidifier. The controller can decrease the desired humidity level by optionally changing a heater plate power set point or a heater plate temperature set point. These two parameters may be used in addition or in alternative to a chamber outlet set point. The controller may be configured to, if the inlet temperature exceeds a threshold, bound or cap a chamber outlet temperature set point such that the amount of humidity generated by the humidifier is capped to account for the increased humidity in the ambient air. The capped chamber outlet temperature set point may define a maximum allowable temperature set point. The controller of the humidifier is configured to remain below the capped chamber outlet temperature set point (i.e. the maximum allowable temperature set point). Additionally or alternatively, the power provided to the heater plate may be capped or bounded if the inlet gases temperature exceeds a threshold to define a maximum allowable heater plate power set point. The controller may also cap or bound the heater plate temperature set point if the inlet gases temperature exceeds a threshold. The capped heater plate temperature set point defines a maximum allowable heater plate temperature set point for the condition (i.e. mode) when the inlet gases temperature exceeds the threshold. The threshold may be a temperature threshold. This process may enable the humidifier to maintain and/or deliver a therapeutic level of humidity while reducing condensation that may form in the inspiratory tube and/or patient interface as a result of additional humidity in the incoming gas. Thus, the systems and methods described herein can account for different incoming humidity levels in a respiratory assistance system and improve patient comfort by reducing rain out when the incoming gas has a humidity greater than a dry gas.

The humidifier and/or humidifier controller disclosed herein may be configured to control a humidifier to operate in two modes, a first mode being a relatively cold and/or low humidity inlet gases mode and a second mode being a relatively hot and/or high humidity inlet gases mode e.g. ambient air. The mode of operation being controlled can be based on the temperature of the inlet gases. If the temperature of the inlet gases (or inlet temperature) is below a threshold, the humidifier functions in a first mode. If the temperature of the inlet gases exceeds a threshold, (that is, the inlet temperature i.e. inlet gases temperature exceeds a threshold) the controller operates in a second mode. The second mode reduce the humidity output of the humidifier. This can be achieved by capping or bounding the chamber outlet temperature set point, in order to reduce the amount of humidity generated by the humidifier. Put another way, the chamber outlet temperature set point may be bounded or capped based on the inlet temperature of the gases to define a maximum allowable chamber outlet set point. The humidifier controller is configured to modify the maximum allowable chamber outlet set point based on the determined inlet temperature. The controller is configured to control the heater plate power to ensure the gases temperature is below the maximum allowable chamber outlet set point. Additionally or alternatively, the controller may cap or bound the heater plate temperature set point or heater plate power in order to reduce or cap or further reduce or cap the humidity generated in the second mode as compared to the first mode. The second mode can thus compensate for humidity present in the inlet gases (for example, where the inlet gases are ambient air that has relatively high humidity).

The humidifier and methods of use described herein can be used to provide high flow, non-invasive, invasive, and/or other therapies. The humidifier can be operated in invasive mode, non-invasive mode, high flow mode, or other modes. The humidifier can operate with various patient interfaces such as, for example, an endotracheal tube (ET tube), full face mask, nasal mask, nasal cannula, nasal pillows, sealed prongs, or any other interface. Other desired humidity levels may be possible and other types of therapy systems may be used. The chamber outlet temperature set point can be adjusted according to the therapies provided and the desired humidity levels.

Example Humidifier

FIG. 1 shows a schematic of an example respiratory assistance system 100. As illustrated, the respiratory assistance system 100 includes a humidifier 104, a gas source 102, a patient interface 116, and an inspiratory conduit 106 configured to transport respiratory gases from the humidifier 104 to the patient interface 116. The gas source 102 and the humidifier 104 may be in separate housings, or optionally may be co-located, within the same housing, and/or included in a single apparatus. The respiratory assistance system 100 includes an optional expiratory conduit 120 configured to transport gases from the patient interface 116 to the gas source 102 and an optional wye-piece 114 configured to connect the inspiratory conduit 106 and the expiratory conduit 120 to the patient interface 116. The respiratory assistance system 100 may not include the expiratory conduit 120 or may include an exhalation port. The operating parameters of the respiratory assistance system 100 may need to be adjusted depending on whether an expiratory conduit or an exhalation port is included. In one example the humidifier is configured to operate with multiple operating parameters, the operating parameters being changeable to allow the humidifier to operate in various configurations e.g. in a single limb configuration (i.e. an inspiratory conduit only) or a dual limb configuration (i.e. an inspiratory conduit and an expiratory conduit)

As illustrated, the gas source 102 includes a ventilator 124, which may include a blower or alternatively a turbine. The gas source 102 may also include other mechanisms to deliver or push a flow of respiratory gases to the humidifier 104, such as a valve arrangement or a pump. The gas source 102 in FIG. 1 is an example room entraining or ambient air entraining ventilator. The gas source 102 may include an inlet 122 through which ambient air is drawn into the gas source 102, for example, by the ventilator 124. The gas source 102 may optionally include a controller 126 configured to control the operation of the ventilator 124. The gas source 102 may optionally include a user interface 132 that can provide information regarding user input to the controller 126. The controller 126 can control the operation of the ventilator 124 based on information provided by the user interface 132 and/or based on other information, for example but not limited to, feedback from the ventilator 124, such as from a sensor associated with the ventilator 124. Instead of drawing ambient air, the inlet 122 can be connected to a supply of dry gas, for example, a gas canister or tank. These types of ventilators can be referred to non-entraining ventilators and may be controlled by one or more valves such as proportional valves. The valve or valves may be controlled by a controller, such as the controller 126.

The humidifier 104 may include a base unit, humidification chamber 134 and a heater plate 136. The heater plate 136 is positioned on the base unit. The humidification chamber 134 may be configured to hold a volume of water W or other suitable liquid. The humidification chamber 134 is positioned on the base unit and in contact with the heater plate 136. The chamber 134 is removable from the base unit. The heater plate 136 may be configured to heat the volume of water W and respiratory gases within the humidification chamber 134, which may increase the temperature of the respiratory gases and may create vapor from the volume of water W that is taken up by the respiratory gases. The heater plate 136 is a plate shaped member. In one example the heater plate 136 comprises a metal plate and a heating element positioned in contact with the heating element. The heating element is positioned within the metal plate. The heating element comprises a substrate with an electrical wire wrapped around the substrate. The humidification chamber 134 may include a chamber inlet 111 and a chamber outlet 112. The inspiratory conduit 106 may be configured to be connected to the chamber outlet 112, such that heated and humidified respiratory gases may be transported by the inspiratory conduit 106 from the humidification chamber 134 to the patient interface 116 and then delivered to a patient P. Gases exhaled by the patient P into the patient interface 116 may optionally be returned by the expiratory conduit 120 to the gas source 102. The respiratory assistance system 100 may not include the expiratory conduit 120 and thus gases exhaled by the patient P into the patient interface 116 may be vented to the atmosphere, such as directly, or optionally through an exhalation port.

The humidifier 104 may include a controller 130 that can control, for example but not limited to, the operation of the heater plate 136. The controller 130 is preferably disposed within the base unit. When the humidifier 104 and the gas source 102 form an integrated device, the controller 126, 130 may be the same hardware processor or separate processors. The controller 130 in one example may be a microprocessor. The humidifier 104 may also include a user interface 140 for providing and/or receiving information regarding user input to the controller 130. The user interface 140 may be located on the base unit. The humidifier 104 further includes an inlet temperature sensor 113. The inlet temperature sensor 113 may be configured to detect the temperature of gases entering the humidifier. The inlet temperature sensor 113 may measure a characteristic of the ambient air near the location of the inlet temperature sensor 113, such as a temperature of the ambient air. The inlet temperature sensor 113 can also be a temperature sensor located at or near the chamber inlet 111. The temperature sensor at the chamber inlet 111 can optionally measure both temperature and flow rate of the air coming in from the gas source 102. This measurement can provide an indication of ambient conditions. In one example the inlet temperature sensor 113 may be a thermistor. Additionally and/or alternatively, the respiratory assistance system 100 may include more than one sensor located at or near the chamber inlet 111. The inlet sensors can include a temperature sensor and a separate flow sensor. The one or more inlet sensors can be located at any location from the gas source 102 to the humidification chamber 134. The one or more outlet sensors 110 and the one or more inlet sensors may be integrated with the humidification chamber 134. The controller 130 may receive information regarding a characteristic of the ambient air near the location of the inlet temperature sensor 113 from the inlet temperature sensor 113. The controller 130 may be configured to control the operation of the heater plate 136 based on information provided by the user interface 140, based on information provided by the inlet temperature sensor 113, and/or based on other information, for example but not limited to, feedback from the heater plate 136, such as from a temperature sensor 146 located at or near the heater plate 136. The controller 130 may be configured to determine an amount of power, or a power duty cycle, to provide to the heater plate 136 such that the heater plate 136 delivers a desired amount of heat to respiratory gases and the volume of water W within the humidification chamber 134. In the illustrated example, the humidifier does not include a hygrometer and only includes temperature sensors at the inlet, outlet and on the heater plate and an optional flow sensor at the outlet. The absence of a hygrometer can make this humidifier cheaper than a humidifier that includes one or more hygrometer since temperature sensors can be cheaper.

The respiratory assistance system 100 may include one or more outlet sensors 110 that are associated with the chamber outlet location 112. The one or more outlet sensors 110 may also be located at or near the chamber outlet 112. The outlet sensors 110 can include two sensors: a temperature sensor and a flow sensor. The temperature sensor can be a thermistor (such as a heated thermistor). The thermistor can also be used as a flow sensor. Accordingly, there may be a single sensor 110 at or near the chamber outlet 112. Other types of temperature sensors and flow sensors that can work in a respiratory assistance system 100 may also be used. The outlet sensor(s) 110 may be located at the chamber outlet 112, at the inspiratory conduit 106 near the connection between the chamber outlet 112 and the inspiratory conduit 106, or at another suitable location downstream of the humidification chamber 134. The controller 130 may receive information from the outlet sensor(s) 110 regarding a characteristic of respiratory gases flowing past the location of the outlet sensor 110. The controller 130 may be configured to control the operation of the heater plate 136 based on information provided by the outlet sensor(s) 110, instead of or in addition to other sources of information as previously described.

An outlet sensor 110 may be integrated into the heater base (i.e. base unit) or may be disposed on an optional cartridge that can be removably attachable to a vertical portion of a heater base (i.e. a base unit). The sensors may be insertable into the inlet port and outlet port as the chamber 134 is positioned in an operative position on the heater base. The chamber inlet and outlet may include openings that correspond to the inlet temperature sensor 113 and outlet sensor 110 to receive the sensors. The sensor openings in the chamber may include polymer covers that are configured to cover the sensor tip as the sensors are inserted into the gases path such that the sensors do not need to be (re)sterilized, since the sensors are not actually in contact with the gases.

Respiratory gases flowing through the inspiratory conduit 106 may lose heat through the walls of the inspiratory conduit 106, which may reduce the temperature of the respiratory gases and may cause condensation to form within the inspiratory conduit 106. The inspiratory conduit 106 may include a conduit heater 144 configured to heat the inspiratory conduit 106 to reduce or prevent this loss of heat. The controller 130 may be configured to control the operation of the conduit heater 144 based on one or several sources of information as previously described. In particular, the controller 130 may be configured to determine an amount of power, or a power duty cycle, to provide to the conduit heater 144 such that the conduit heater 144 delivers a desired amount of heat to the inspiratory conduit 106. The conduit heater may be disposed into the wall of the conduit or may be disposed within the lumen of the conduit.

The respiratory assistance system 100 may include one or more conduit sensors 142 located within the inspiratory conduit 106. The conduit sensor(s) 142 may be located at the inspiratory conduit 106 near the connection between the inspiratory conduit 106 and the wye-piece 114, at the connection between the inspiratory conduit 106 and the patient interface 116 if the inspiratory conduit 106 is connected directly to the patient interface 116, or at the wye-piece 114 or the patient interface 116. The conduit sensor(s) 142 may measure a characteristic of respiratory gases flowing past the location of the conduit sensor 142, such as a temperature of the respiratory gases. The conduit sensor 142 can include a temperature sensor. The conduit sensor 142 can also include a separate flow sensor. The conduit sensor 142 can include an integral flow and temperature sensor that is capable of measuring both the temperature and flow rate such as described herein. The controller 130 may receive information regarding a characteristic of respiratory gases flowing past the location of the conduit sensor 142 from the conduit sensor 142. The controller 130 may determine the flow rate of respiratory gases flowing past the conduit sensor 142. The controller 130 may be configured to control the operation of the conduit heater 144, and/or the operation of the heater plate 136, based on information received from the conduit sensor 142, instead of or in addition to other sources of information as previously described. The conduit sensor may be integrated into the conduit and extend into the gases pathway defined by the conduit. Further, the conduit sensor's wires may be integrated into the wall of the conduit or extend along the conduit.

Respiratory gases may also lose heat through the walls of the patient interface 116, the wye-piece 114, and/or any other respiratory system component that may connect the patient interface 116 to the inspiratory conduit 106. One or more of the patient interface 116, the wye-piece 114, and any other respiratory system component that may connect the patient interface 116 to the inspiratory conduit 106 may include an associated heater and/or an associated sensor. The controller 130 may receive information from such an associated sensor regarding a characteristic of respiratory gases flowing past the location of the sensor. The controller 130 may use information received from such an associated sensor to control the operation of the respective associated heater.

One or more of the patient interface 116, the wye-piece 114, and any other respiratory system component that may connect the patient interface 116 to the inspiratory conduit 106 may not include an associated heater and/or an associated sensor. The controller 130 may use an estimate of the heat lost by respiratory gases flowing through unheated respiratory system components to control other heaters associated with the humidifier 104, such as the heater plate 136 and/or the conduit heater 144. The controller 130 may calculate such a heat loss estimate for unheated respiratory system components based on other received information, such as, but not limited to, information received from the outlet sensor 110, the conduit sensor 142, the inlet temperature sensor 113, and/or the user interface 140, and/or based on information retrieved from a data storage device, which may be located in the controller. The data received from the sensors described herein can also be stored in the data storage device.

The humidifier 104 may be used in the respiratory assistance system 100 to deliver heated and humidified respiratory gases to the patient P for multiple types of respiratory therapies, including but not limited to invasive ventilation therapy, non-invasive ventilation therapy, high flow therapy, BiPaP therapy, Continuous Positive Airway Pressure therapy, or other respiratory assistance therapy. The humidity conditions of the respiratory gases provided to the humidifier 104 by the gas source 102 may vary. For example, the type of the gas source 102 used in the respiratory assistance system 100 may depend on the type of respiratory therapy, respiratory system configurations, location of use (such as home or hospital), or availability of different gas supplies. Gases from different supplies may have different characteristics, including temperature and humidity. Ambient air, in particular, ambient air in tropical weather and/or during summer time can have a higher humidity than gas obtained from a compressed gas tank or bottle. It may be beneficial to adjust the operating parameters of the respiratory assistance system 100 using a control system 220 (described below) such that the patient receives comfortable care, for example, with reduced and/or minimized rain out in the inspiratory tube and/or patient interface while still receiving adequately humidified gases in spite of different supply gas characteristics. The control system may be able to automatically adjust operating parameters based on an inference of whether the supply gas is dry or ambient. The operating parameters may include certain temperature set points described below. Additionally or alternatively, the operating parameters may be a dew point, humidity output of the humidifier, or other suitable parameter.

Figure 2A:
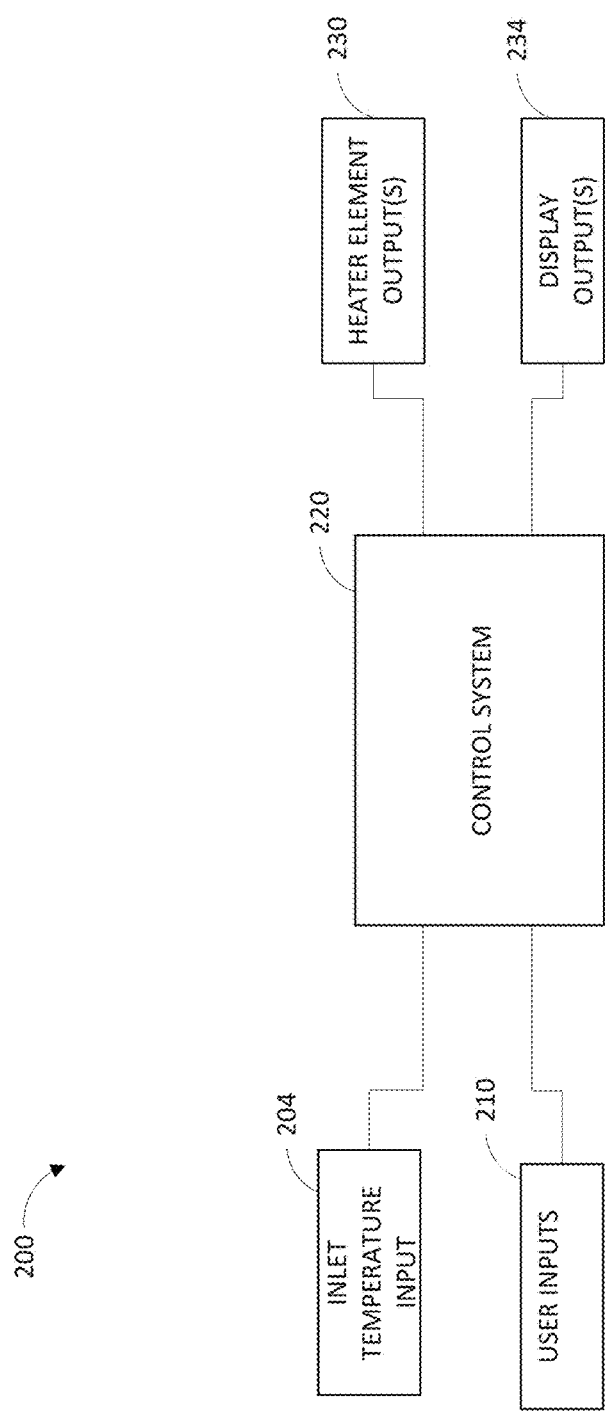
FIG. 2A illustrates a block diagram of an example control system interacting with and/or providing control and direction to components of a respiratory assistance system.

FIG. 2A illustrates an example control system 220 for detecting the input conditions of the gas source 102 and automatically controlling the components of the respiratory assistance system 100 described above to change the output conditions of the gas delivered to the patient. The control system 220 can generate outputs configured to control operation of components of the respiratory assistance system 100, based on the inputs received. The control system can generate a heater element output 230 so as to change a temperature set point of one of the heating elements, such as the heater plate 136, to control the output conditions of the gas delivered to the patient. The control system 220 can also change the operation or duty cycle of the heater plate. The control system 220 may not require direct communication between the humidifier 104 and the gas source 102 for determination of the input conditions. The control system 220 can also generate other outputs, such as a flow control output so as to change a flow rate of the gases, and/or generate output 234 to a display. The user inputs 210 can be received through a user interface e.g. a touchscreen. The user inputs may be a selection of a particular mode corresponding to the type of therapy (for example invasive ventilation, non-invasive ventilation, or high flow therapy such as for example Fisher & Paykel Healthcare's Optiflow therapy). Further user inputs may specify a desired dew point deliver to the patient, that is, a desired humidity value. For example, each mode may comprise a plurality of preset desired dew point values (such as 31° C., 29° C., 27° C., or otherwise) that can be selected by the user. The selected dew point causes the controller to control the heater plate and/or the heater wire in the inspiratory conduit to deliver saturated gases at a selected temperature (i.e. a selected dew point).

Figure 2B:
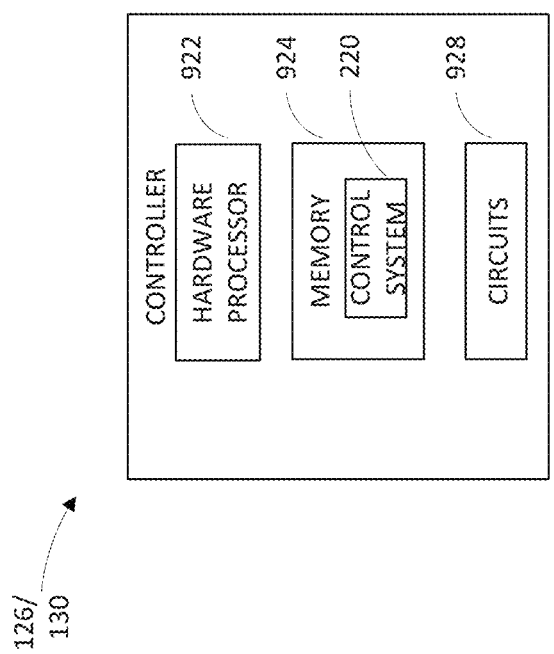
FIG. 2B illustrates a block diagram of an example controller.

The control system 220 can include programming instructions described herein for detection of input conditions and control of output conditions. The programming instructions can be stored in a memory 924 of the controller 126, 130 as shown in FIG. 2B. The programming instructions can include instructions corresponding to the processes and functions described herein. The control system 220 can be executed by a hardware processor 922 of the controller 126, 130. The programming instructions can be implemented in C, C++, JAVA, or any other suitable programming languages. Some or all of the portions of the control system 220 can be implemented in application specific circuitry 928 such as ASICs and FPGAs.

As illustrated in FIG. 2A, the control system 220 can receive inputs from multiple components of the respiratory assistance system 100. Other types of input may also be present. A humidity sensor may or may not be included. The controller may also receive inputs from the various sensors of the system. Additionally or alternatively, the humidifier may receive signals or inputs from a user device, such as a mobile phone or a tablet.

Excess Humidity in Room Entrained Air

Figure 3:
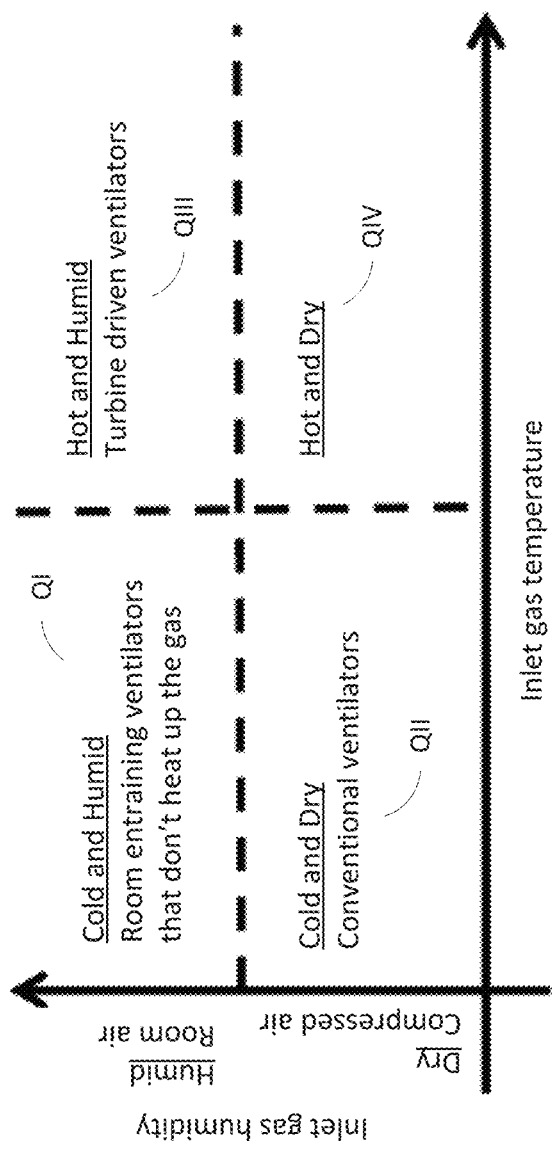
FIG. 3 illustrates potential types of gases at an inlet of a humidification chamber.

FIG. 3 illustrates potential gas conditions at an inlet of a humidification chamber. Without knowledge of the inlet humidity conditions, a humidifier can deliver close to desired humidity level in at least three out of four types of gas conditions, as shown in FIG. 3: cold and humid (QI), cold and dry (QII), and hot and dry (QIV). "Cold" may correspond to a temperature that is about ambient temperature or below ambient temperature, which can be about 24° C., and 'Hot' may correspond to an elevated temperature above ambient. In the illustrated example of FIG. 3, cold is considered below 24° C. and hot is considered equal to or more than 24° C. In some examples, inlet temperatures above 24° C. can be caused by heat generated by turbines within room air entraining ventilators. Ambient air passing through the turbine of a room entraining ventilator are heated above ambient temperature due to the turbine spinning the gases. In some examples, the generated heat may be in addition to an elevated ambient temperature. Compressed air (for example, from a gas tank) is generally considered cold and dry because it is not humidified (for example, has humidity below ambient) and is generally below 24° C., (for example, may have a temperature of 18° C.).

A humidifier as described herein may modify a maximum amount of added humidity i.e. the described humidifier may modify the amount of humidity added based on the inlet temperature of gases. In some examples, when an inlet temperature is low (that is, the gas is cold as shown in quadrants I and II in FIG. 3), a relative humidity (RH) of gas at the chamber outlet may be near saturation regardless of the inlet gas humidity level. This is because the heater plate of the humidifier may heat up and add humidity to the gas. Put another way, the temperature differential between the inlet temperature and the outlet temperature can be large enough so that the humidifier can add enough humidity to saturate the gases.

On the other hand, in examples where the chamber inlet temperature is high or sufficiently elevated from ambient condition (that is, the gas is hot as shown in quadrants III and IV in FIG. 3), the RH level at the chamber outlet may reduce. This is because the heater plate may have a safety temperature limit such that it cannot heat beyond a certain temperature. Thus, the heater plate may have a smaller buffer or range in which to heat up and add humidity before reaching the maximum allowable chamber outlet temperature set point. An example of the maximum allowable chamber outlet temperature set point can be about 36° C.

Additionally or alternatively, at higher temperatures with the same level of humidity, the ability of water to evaporate from a water surface may be reduced due to the increased vapor pressure of the humid gas on the water surface. Accordingly, different inlet humidity levels can have a different effect on the outlet humidity level.

In another example, delivery of hot and (relatively) dry gas to the patient may cause irreversible damage to the patient's airways. Accordingly, in order to help prevent this issue, the system may avoid delivering hot and dry gases by effectively treating an incoming hot and dry gas as having a cold and dry condition as the humidity is low in an incoming hot and dry gas. This assumption is made so that humidity can be increased as the incoming gases are heated by the heater plate as the gases pass through the humidification chamber.

The humidifier generally adds more heat and humidity to incoming gases. Depending on the temperature and humidity of the incoming gases, this can result in over humidification and/or over heating in some cases. For example, air that is drawn in by a room air entraining ventilator can include some amount of humidity. The humidity of room air can be greater than from a compressed gas source such as gas bottle or wall supplied gas. Additionally, as described above, the room air entraining ventilator commonly uses a blower or a turbine, which can undesirably heat up the gas. As the increased temperature of the gas can increase the dew point, this excess heat can result in the room entrained air being further humidified before it enters a humidification chamber.

Figure 4A:
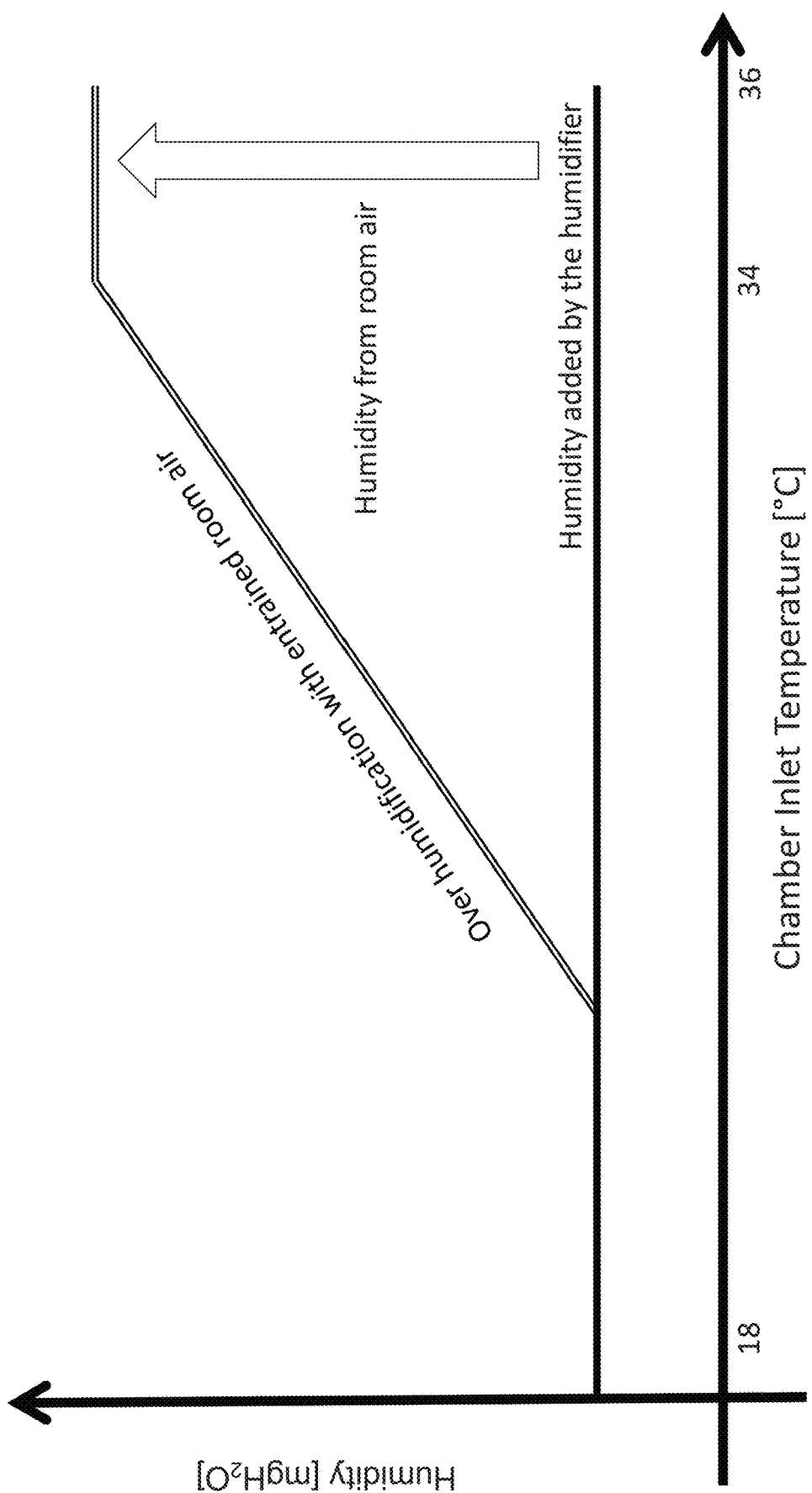
FIG. 4A illustrates an example graph of actual humidity in outlet gases as a function of inlet temperature for a room air entraining ventilator.

FIG. 4A illustrates an example graph of a dew point of outlet gases as a function of inlet temperature for a room air entraining ventilator when the humidifier assumes that all incoming gas is dry. The dew point corresponds to an absolute humidity value. In particular, FIG. 4A illustrates how a humidifier may add unneeded humidity in the case of room entrained air because a humidifier may not account for humidity already present in room entrained air. As described above, the humidifier may be able to reliably deliver the desired humidity level across a range of different chamber inlet temperatures using a gases source. The solid black line in FIG. 4A is the humidity added by the chamber and represents the humidity added by the chamber when cold, dry gases are used. The double black line in FIG. 4A shows the cumulative humidity when ambient air is entrained (in particular, the chamber humidity plus the ambient humidity). Under dry air source conditions, the desired humidity level may be about the same as the level of humidity added by the humidifier. However, when used with a room air entraining ventilator, the additional humidity from the room air can cause the humidifier to deliver above the desired or target humidity level, as illustrated in FIG. 4A, and increase the level of condensation.

Figure 4B:
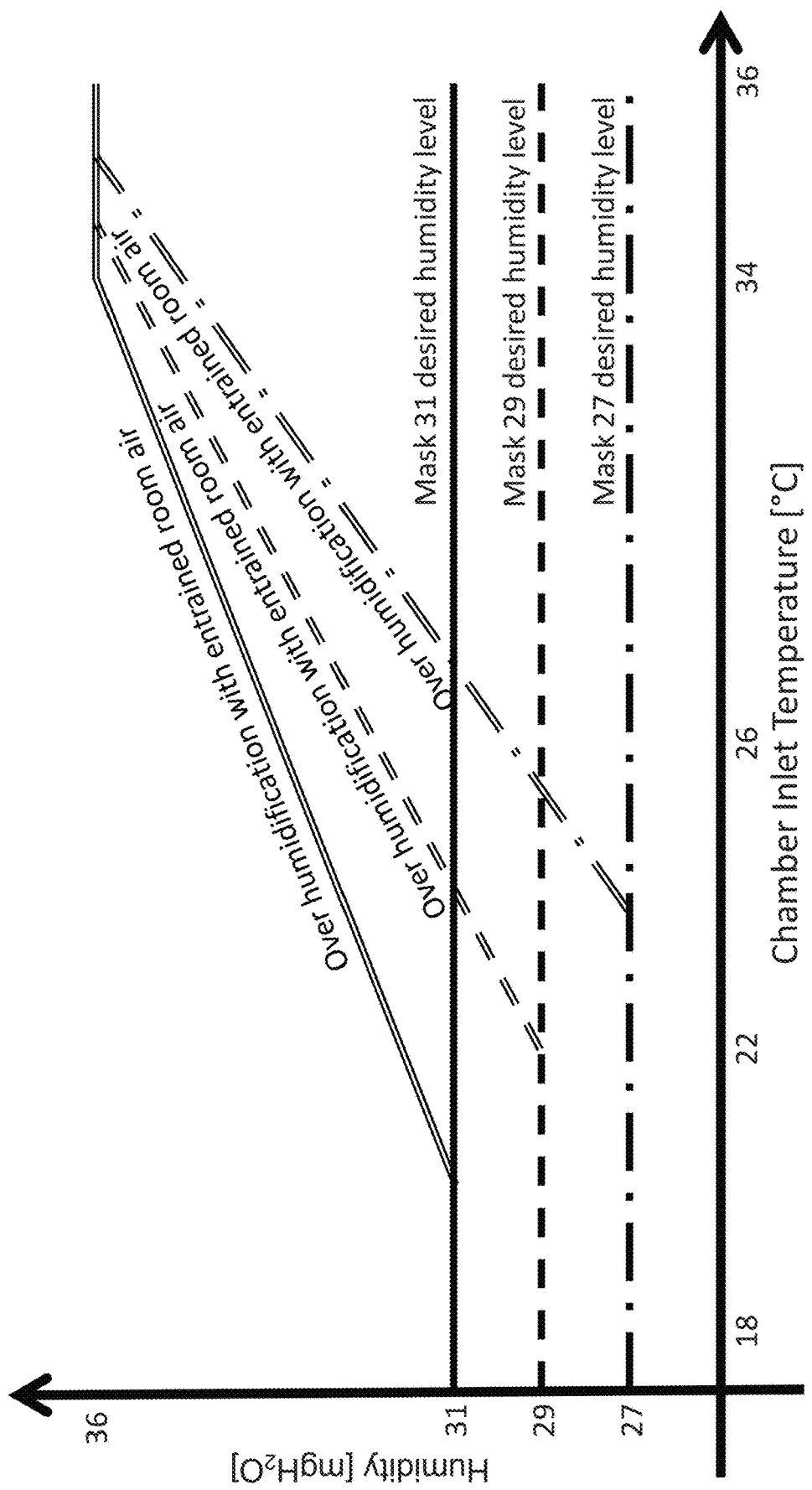
FIG. 4B illustrates an example graph of actual humidity in outlet gases as a function of inlet temperature for a room air entraining ventilator for different non-invasive user settings of a humidifier.

Over humidification can occur at different chamber inlet temperatures for room entrained air based on the desired humidity level. FIG. 4B illustrates an example graph of humidity of outlet gases as a function of inlet temperature for different user settings of a room air entraining ventilator. For example, as illustrated in FIG. 4B, a 31° C. humidifier mode (shown as the Mask 31 desired humidity level) can begin to over humidify at a chamber inlet temperature of around 20° C. A 29° C. humidifier mode (shown as the Mask 29 desired humidity level) can begin to over humidify at a chamber inlet temperature of around 22° C. A 27° C. humidifier mode (shown as the Mask 27 desired humidity level) can begin to over humidify at a chamber inlet temperature of around 24° C. The solid lines in FIG. 4B represent the humidity (or dew point) delivered to the patient. Mask 31, Mask 29, and Mask 27 lines represent the desired dew points to be delivered to a patient in the "Mask mode". The desired dew points correspond to an amount of humidity delivered to the patient. Mask mode represents non-invasive therapy. More specifically "Mask mode" denotes respiratory therapy delivered using a sealing mask e.g. a full mask. Mask mode denotes pressure therapy e.g. BiLevel pressure therapy or constant positive airway pressure (CPAP) or other non invasive ventilation modes. The over humidification curves (lighter double lines) illustrate the additional humidity, that is, over humidification due to the ambient humidity when ambient air is used in Mask mode at the 3 different set points. The upwardly oriented lines represent the increased dew point of the gases that is, gases delivered at a higher humidity that what is desired. The controller in a first mode operates on the assumption that dry gases are being delivered, and hence if ambient air is used in this first mode there is often over humidification. The systems disclosed herein causes the humidifier to function in a second mode when the inlet temperature exceeds a threshold to reduce over humidification.

Figure 5A:
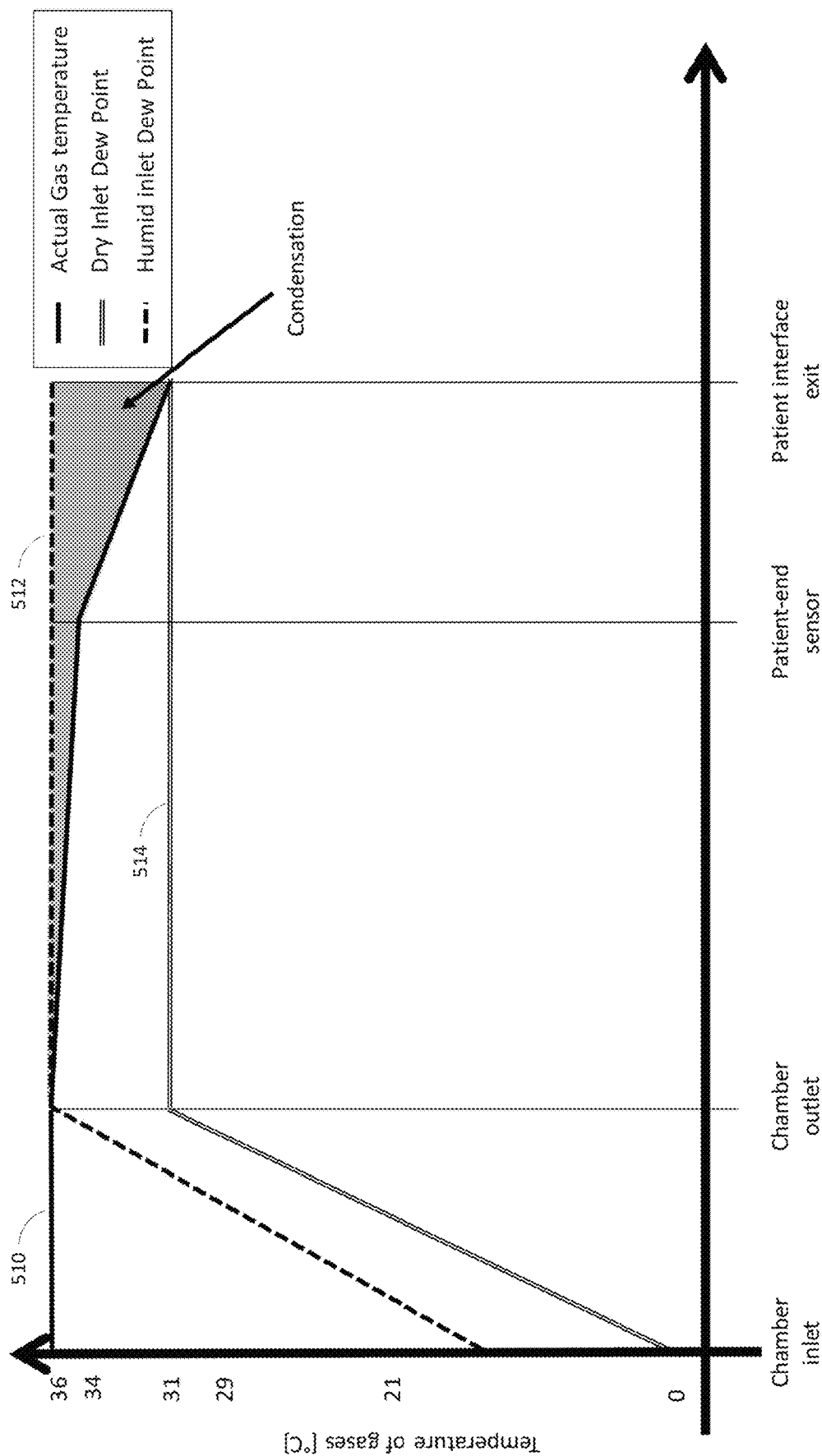
FIG. 5A is a graph showing example effects of additional room air humidity at an inlet temperature of 36° C.
Figure 5B:
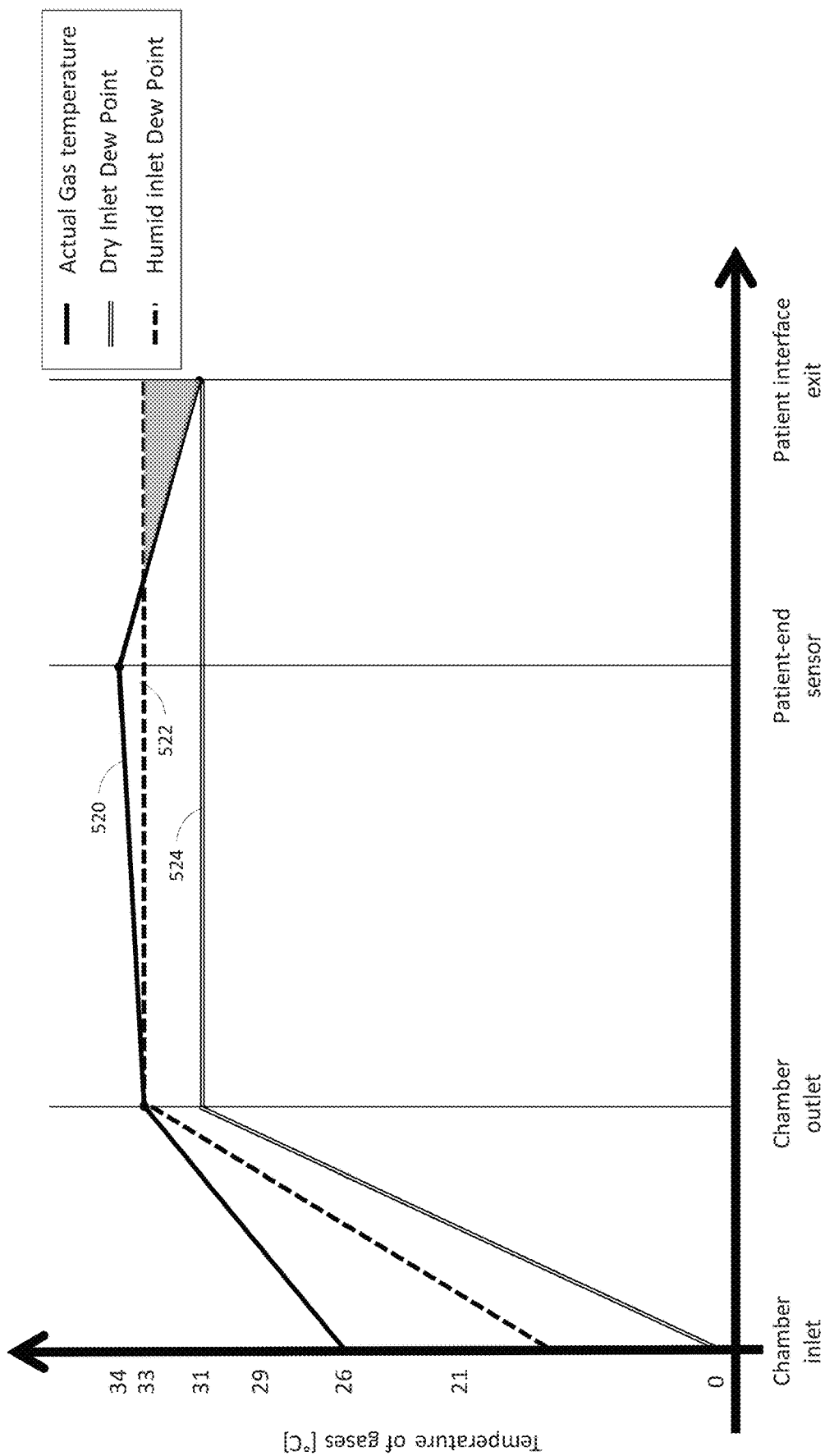
FIG. 5B is a graph showing example effects of additional room air humidity at an inlet temperature of 26° C.
Figure 5C:
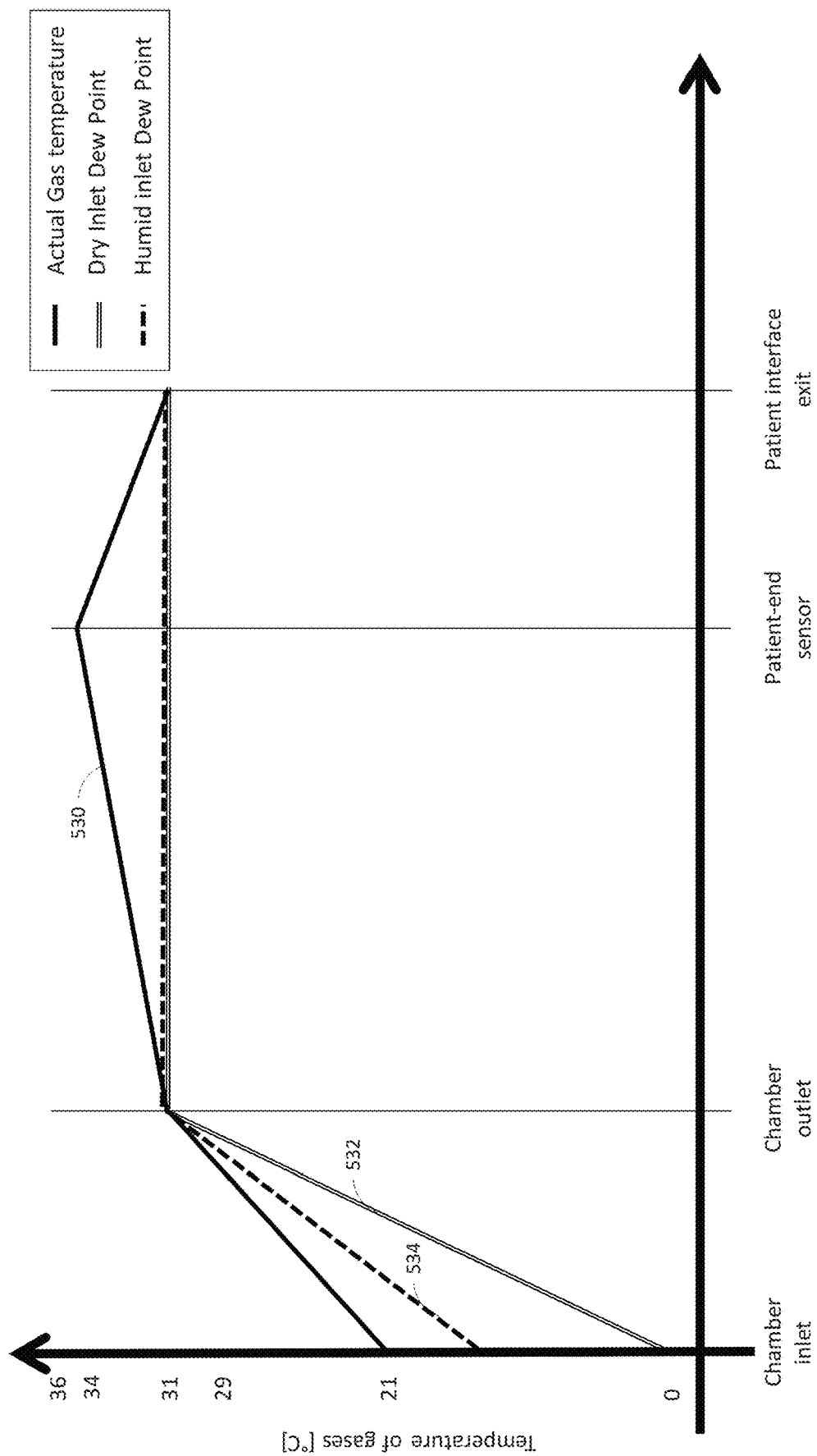
FIG. 5C is a graph showing example effects of additional room air humidity at an inlet temperature of 21° C.

FIGS. 5A-5C represent three different use cases of the humidifier at three different inlet gas temperatures. FIG. 5A is a graph showing the effects of additional room air humidity at an inlet temperature of 36° C. (in other words, at an actual inlet gas temperature of 36° C.). As illustrated in FIG. 5A, an incoming gas temperature 510 may be relatively hotter than ambient. For example, ambient temperature may be 24° C. and an incoming gas temperature may be 36° C. (that is, a hot incoming gas). In order to try to achieve the desired humidity level using a dry gas source, a humidifier may set a maximum chamber outlet set point to a target humidity corresponding to a dew point of, for example, 31° C. as illustrated by line 514. Line 514 may be the first function (or first mode) of operation when the humidifier assumes that the incoming gases are dry gases. In normal operation of the humidifier, the hot and dry incoming gas can pick up the desired level of humidity corresponding to a chamber outlet temperature that corresponds to a patient end desired dew point of, for example, 31° C. as it passes over an evaporating water surface within the humidification chamber. The example value of 31° C. represents a desired dew point at the patient. This desired dew point can be used to calculate and/or set a chamber outlet set point temperature and/or a patient end set point temperature. Further, the chamber outlet set point can be used to control the heating/power of the heater plate to achieve the chamber outlet set point. However, when the humidifier is used with a room air entraining ventilator, the hot incoming gas, which already contains more humidity than a dry gas, may over humidify as it picks up humidity in the humidification chamber having an actual humidity equivalent to a 36° C. dew point as illustrated by line 512. This over humidification can result in unwanted condensation at the patient interface and can also result in condensation within the conduit.

Condensation may occur because the temperature of the gases reduces below the actual dew point of the gases. For example, condensation may occur because the actual dew point of the gases in the respiratory assistance system can be greater than the desired humidity level (such as line 514 corresponding to a 31° C. dew point in this example) due to additional room air humidity. In the example shown in FIG. 5A, the actual dew point at the chamber outlet may be, for example, 36° C., shown by line 512. The duty cycle of an inspiratory wire in a respiratory assistance system may be controlled in such a way as to enable gases to cool from the chamber outlet temperature (for example, 36° C. shown in FIG. 5A) to a patient end temperature (for example, 34° C. shown in FIG. 5A). When the gases cool to the patient end temperature, water vapor that can no longer be contained in the gases with the lower dew point, for example, of 34° C. in this example, will condense into a liquid. This condensation is represented by the grey area in FIG. 5A. FIG. 5A shows a first mode of operation (or normal operation on the assumption of dry gases being used). The desired patient dew point of 31° C. may be used to define a temperature at the patient end sensor and a chamber outlet set point. In this mode, the humidifier may be controlled to achieve an example dew point of 34° C. at the patient end. An outlet temperature of the gases may be 36° C. Because this outlet temperature is greater than the chamber outlet temperature setpoint and/or the temperature that is desired at the patient end, which is 34° C. in this example, the system will be configured to cool the gases as the gases travel from the chamber outlet to the patient end, shown by line 510 between the chamber outlet and patient end. However, the dew point of the gases may also correspond to 36° C. at the chamber outlet. The dew point of the gases can never be higher than the actual temperature of the gases. Therefore, as the gases cool down between the chamber outlet and patient end, the dew point of the gases will also decrease and can be equivalent to, but not exceed, line 510. As mentioned above, the water vapor that can no longer be contained in the gases with the lower dew point of 34° C. will condense into a liquid. This condensation is represented by the grey area in FIG. 5A. FIG. 5A also illustrates further cooling that may occur at a patient interface region, which may be any region beyond the distal end of the inspiratory tube. These regions may include patient interfaces such as an endotracheal tube for invasive respiratory therapy or a full face mask for non-invasive therapy.

When operating with bottled or dry gas, a patient-end temperature can be calculated and targeted to be greater than the dew point corresponding to the desired humidity level. For example, a patient-end temperature of 34° C. may be targeted, which is 3° C. above the desired 31° C. dew point temperature. This targeting is to account for a temperature drop as the gases travel across the patient interface. Because patient interfaces are usually not heated, the gases generally cool across patient interfaces. While a 3° C. temperature drop may be calculated in the operation of a respiratory assistance system, any suitable temperature drop may be used. As shown in FIG. 5A, because the gases are below the actual dew point, more condensation forms in the patient interface as the gases further cools across the patient interface down to 31° C. This causes discomfort to the patient and may disrupt therapy as the patient takes off the patient interface and/or inspiratory tube to dispose of the condensation. Further, the additional condensation can also be a safety risk because condensation inside the patient interface can lead to an increased drowning risk for the patient or may cause discomfort to the patient.

FIGS. 5B-5C show the effects of additional room air humidity at an inlet temperature of 26° C. and 21° C. respectively. In the case of a gas with an inlet temperature of 26° C. (gas temperature is shown by line 520) as shown in FIG. 5B, the actual dew point at the chamber outlet can be 33° C., as shown by line 522, and the desired dew point at the chamber outlet may be 31° C., as shown by line 524. In such a case, condensation may form in the patient interface, shown by the shaded area in FIG. 5B. In the case of an inlet temperature of 21° C. (gas temperature is shown by line 530) as shown in FIG. 5C, the actual (line 534) and desired (line 532) dew point at the chamber outlet may be 31° C. In such a case, as described above, condensation may not form in the inspiratory tube or in the patient interface because the inlet gas is not hot relative to the ambient air and so the relative humidity of the gas at the chamber outlet may be near saturation regardless of the inlet gas humidity level. In the case shown in FIG. 5C, the temperature of gases is above the dew point and, therefore, no condensation will occur. In FIG. 5C, the dry and humid inlet dew points remain substantially constant between the chamber outlet and the patient interface exit.

Controlling Outlet Humidity as a Function of Inlet Temperature

The control system described herein can minimize or at least reduce condensation levels and improve humidity delivery to the patient through a process of monitoring chamber inlet temperatures. The control system for the humidifier as described is configured to control supplied heater plate power and/or modify a chamber outlet temperature set point or a humidity set point or a heater plate power or temperature set point based on the monitored chamber inlet temperatures to reduce condensation within the conduit and/or the patient interface and/or unheated sections downstream of the conduit. For example, a chamber outlet temperature and/or humidity behavior can operate as a function of chamber inlet temperature. For example the chamber outlet temperature set point may be capped (i.e. bounded) based on the inlet temperature of the gases. In another example the humidity set point or the heater plate temperature set point or heater plate power set point may be capped based on the inlet temperature of the gases The control system may make use of this functional relationship to help ensure that too much excess humidity is not added to the gases through the humidifier. In particular, the functional relationship may assume that incoming gas above a threshold temperature is likely to contain excess humidity. Thus, the control system may modulate the target humidity, for the humidifier to add less humidity to the incoming gas. For example, for a given therapy mode of a humidifier, if a chamber inlet temperature is below a threshold, the desired humidity level range can be delivered to the patient. If chamber inlet temperature exceeds the threshold, the humidity delivered can be decreased to a humidity level range lower than the initial desired humidity level range. The humidity level can be controlled by controlling a chamber outlet temperature set point, a heater plate temperature set point or a heater plate power. For example, the chamber outlet temperature set point may be bounded or capped based on the inlet temperature of the gases, as shown in the flow chart in FIG. 6A and the diagram in FIG. 7. The illustrated examples are based on controlling a chamber outlet temperature set point by capping the chamber outlet temperature set point. Additionally or alternatively, the heater plate set point or heater plate power may be capped or bounded to reduce the humidity output of the humidifier if the inlet temperature exceeds a threshold. Additionally, or alternatively, the humidity level can be controlled by reducing the maximum chamber outlet temperature set point (i.e. maximum allowable chamber outlet temperature set point), such as shown in the flow chart of FIG. 6B and the diagram in FIG. 7. There can be a maximum chamber outlet temperature set point, after which power to the heater plate is disabled. The controller is configured to disable or stop the heater plate if the chamber outlet temperature exceeds the maximum allowable chamber outlet temperature set point. In one example the heater plate power may be bounded or capped based at least in part on the inlet temperature of the gases to define a maximum allowable heater plate power. In a non-limiting example, the controller is configured to modify the maximum allowable heater plate power based at least in part on the determined inlet temperature. The controller is configured to control the heater plate power up to the maximum allowable heater plate power. The controller is configured to control the heater plate power to any heater plate power that may be calculated under/less than the maximum allowable heater plate power. In a further example the heater plate temperature setpoint may be bounded or capped based at least in part on the inlet temperature of the gases to define a maximum allowable heater plate temperature setpoint. In a non-limiting example, the controller is configured to modify the maximum allowable heater plate temperature setpoint based at least in part on the determined inlet temperature. The controller is configured to control the heater plate power up to the maximum allowable heater plate temperature setpoint. The controller is configured to control the heater plate power to any heater plate temperature setpoint that may be calculated under/less than the maximum allowable heater plate temperature setpoint The humidifier may include a second operating mode which sets humidity output or other parameters of the humidifier based on, for example the inlet temperature. In this second mode, the humidifier may control either a chamber outlet set point, a heater plate temperature set point, or a heater plate power based on the inlet temperature. In this second mode of operation, the power to the heater plate may be capped based on the inlet temperature of the gases. The second mode may be activated if the inlet temperature exceeds a temperature threshold. In some examples, a temperature threshold may be a pre-determined threshold. In one example implementation the temperature threshold is 24° C. In one example, in the second mode the chamber outlet set point may be capped (i.e. bounded) if the inlet temperature of the gases exceeds a temperature threshold. In a further example the heater plate temperature set point may be capped (i.e. bounded) if the inlet temperature of the gases exceeds a temperature threshold. The chamber outlet temperature set point may be capped at a maximum allowable chamber outlet if the inlet temperature of the gases exceeds the temperature threshold. The heater plate temperature set point may be capped at a maximum allowable heater plate temperature set point, if the inlet temperature exceeds the temperature threshold. The heater plate power may be capped to a maximum allowable heater plate if the inlet temperature exceeds the temperature threshold. The capped chamber outlet temperature set point or heater plate temperature set point or heater plate power may be modulated (i.e. modified) based on the inlet temperature of the gases. For example these maximum allowable set points may be modified as a function of the inlet temperature in the second mode, when the inlet temperature exceeds the temperature threshold.

Advantageously, using the method described herein, the humidifier controller does not need to directly determine the humidity of the input gas nor does it need to adjust control parameters if a room air entraining ventilator was detected. The described humidifier control method (and humidifier) also does not require any specific sensor configuration or detection method to determine the type of ventilator or gases source connected to the humidifier. Further the humidifier does not require complex and expensive humidity sensors (e.g. hygrometers). Therefore, this control system and method can provide a simpler and more cost-effective solution to reducing condensation levels during operation of a humidifier using room entrained air at least because it does not require a humidity sensor upstream of the humidification chamber.

Figure 6A:
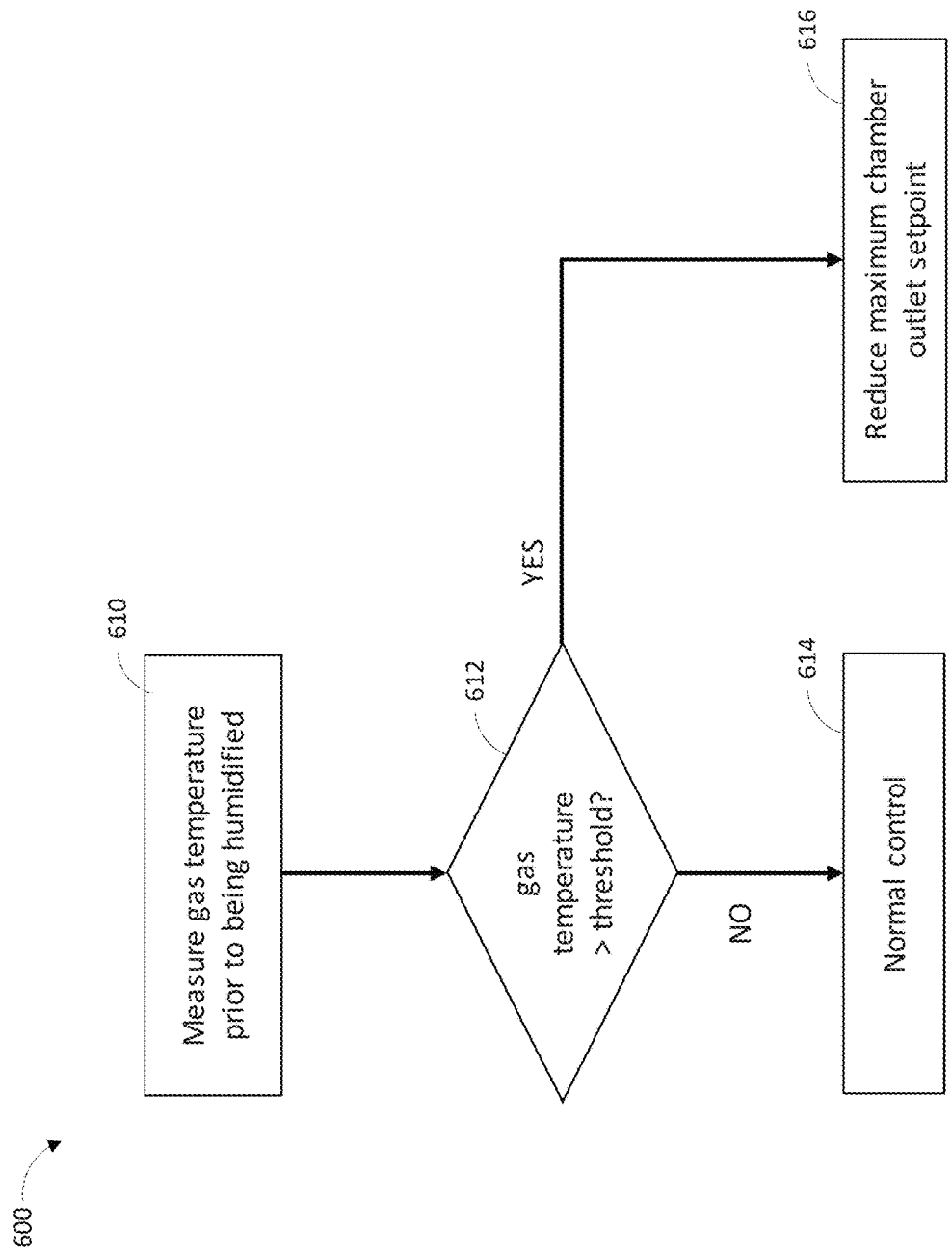
FIG. 6A illustrates an example process of setting a maximum chamber outlet set point based on inlet temperature.

FIG. 6A illustrates an example process 600 of setting a maximum allowable chamber outlet temperature set point using an incoming gas temperature threshold. For example, the process 600 may include a step 610 wherein the system measures the gas temperature of gas in or near the inlet to the humidification chamber, or anywhere in the gases flow path upstream of the humidification chamber. The system may then determine whether the measured gas temperature exceeds a temperature threshold in a decision block 612. If the gas temperature exceeds the threshold, the system may reduce the maximum chamber outlet temperature set point in a step 616. The maximum allowable chamber outlet temperature set point is reduced to a lower value as compared to the maximum allowable chamber outlet temperature set point when the inlet temperature is less than the temperature threshold. Put another way, if the gas temperature (i.e. inlet gases temperature) does not exceed the threshold, then the system may continue under normal operation under a step 614, for example, by maintaining the pre-determined chamber outlet set point and/or the pre-determined power or duty cycle of the heater plate. The step 614 may correspond to a first or normal mode of operation. The step 616 may correspond to a second mode of operation where the humidity at the outlet is capped or bounded. This may be achieved by capping or further capping the chamber outlet set point, capping a heater plate temperature (i.e. heater plate temperature set point), or capping a heater plate power. The capped values are capped based on the inlet temperature exceeding a threshold e.g. a temperature threshold. The capped chamber outlet temperature set point defines a maximum allowable chamber outlet temperature set point. The capped heater plate temperature (i.e. heater plate temperature set point) defines a maximum allowable heater plate temperature set point. The capped heater plate power (i.e. heater plate power set point) is a maximum allowable heater plate power (i.e. maximum allowable heater plate power set point). The capped values may be modulated by the controller as a function of the inlet temperature. The capped values define maximum allowable values in the second mode i.e. when the inlet temperature of gases exceeds the temperature threshold. In one example the maximum allowable set points in the second mode may be lower than a maximum set point in the first mode.

Figure 6B:
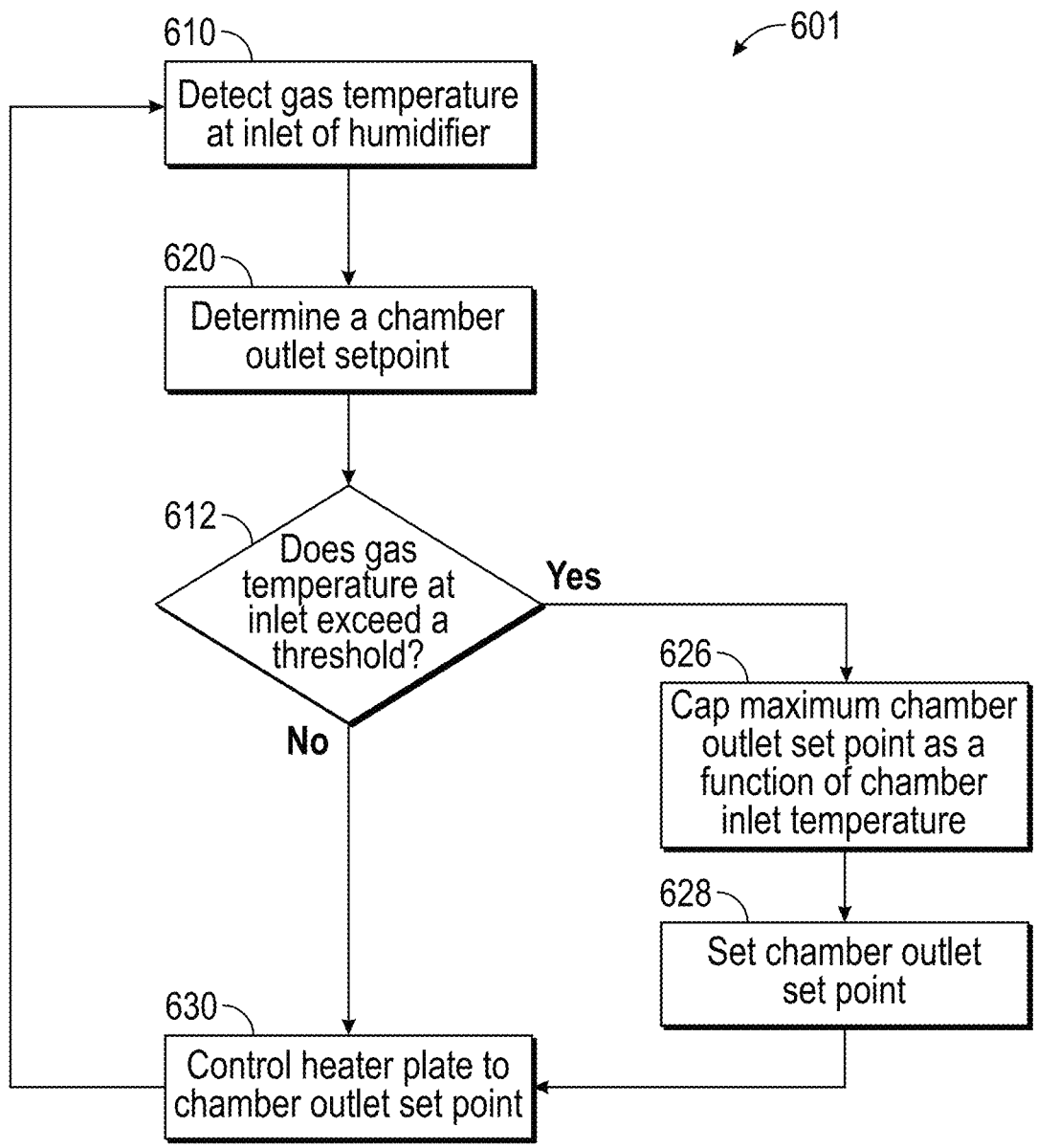
FIG. 6B illustrates another example process of setting a maximum chamber outlet set point based on an inlet temperature.

FIG. 6B illustrates an example process 601 of setting a maximum chamber outlet temperature set point (i.e. a maximum allowable chamber outlet temperature set point), using an incoming gas temperature threshold. For example, the process 601 may include a step 620 wherein the system measures the temperatures of the gases in or near the inlet to the humidification chamber, or anywhere in the gases flow path upstream of the humidification chamber. The system may then determine a chamber outlet temperature set point based on the inlet gases temperature in a step 620. Optionally, other inputs can be used to define the chamber outlet temperature set point in addition to the inlet gases temperature. The system may then determine whether the measured inlet gases temperature exceeds a temperature threshold in a decision block 612. If the inlet gases temperature does not exceed the threshold, the system may control the heater plate in a step 630 to the chamber outlet temperature set point determined in step 620. In one example the chamber outlet temperature set point determined in step 620 may define a maximum allowable chamber outlet temperature set point i.e. define an upper bound for the chamber outlet temperature. If the inlet gases temperature exceeds the threshold, then the system may cap or bound the maximum allowable chamber outlet temperature set point based on the inlet gases temperature in a step 626 i.e. cap or bound the allowable temperature of gases at the chamber outlet. Once the system caps or bounds the maximum allowable chamber outlet temperature set point, in a step 626, then the system may set a new chamber outlet set point temperature in a step 628. Once a new chamber outlet set point temperature is set in a step 628, the system (i.e. the humidifier controller) is configured to control the heater plate in a step 630 up to the chamber outlet temperature set point determined in step 628. The controller may be configured to modulate the chamber outlet temperature set point determined in 628 based on at least the inlet temperature and flow to achieve a desired humidity level. The controller is configured to control the chamber outlet temperature set point such that it does not exceed the maximum allowable temperature set point determined in step 626. The controller is further configured to control the heater plate power based on feedback from a chamber outlet temperature sensor (e.g. sensor 110) such that the temperature of gases does not exceed the maximum allowable chamber outlet temperature sensor.

The chamber outlet temperature in determined in a step 620 may be unbounded in some situations. For example, the chamber outlet temperature in a "normal operation" (or in a first function/mode) is unbounded and can go to a maximum of about 36° C. The maximum of 36° C. may be hard limit meaning if the gases temperature at the chamber outlet exceeds 36° C., the heater plate power is switched off either by a software cut out or a hardware cut out or a combination thereof. Chamber outlet set point may be based on some combination of inlet temperature, heater plate temperature and/or an input from one or more other sensors (for example, an ambient temperature sensor and/or flow). The chamber outlet set point may be capped or bounded in a step 626. For example, in a "new operation" (or in a second function/mode), the maximum outlet temperature possible for a given inlet temperature may be bounded/capped (i.e. capped to define a maximum allowable chamber outlet temperature) so that the amount of humidity generated is limited for that particular inlet temperature.

As described above, the system may measure the gas temperature through an inlet temperature sensor in step 610. The inlet gases sensor could be an inlet gases temperature sensor could be used on the inlet. The inlet temperature sensor may be coupled to an inlet into the humidification chamber such that it can measure the temperature of the gases within the inlet. The temperature sensor can be any sensor configured to measure a gases temperature, such as a thermistor or a probe sensor. However, the temperature sensor need not be directly attached to the inlet and can be near the inlet or on or within the inlet. The gases within the inlet can be any gas entering the humidification chamber that has not yet been humidified by the humidification chamber. These gases can include dry gases, such as bottled gas, or gases that contain excess humidity, such as room entrained gases.

The temperature threshold can include a single temperature threshold or multiple temperature thresholds. For example, in the case of multiple thresholds, the system may determine whether an inlet gas temperature exceeds a first temperature threshold to set a first chamber outlet set point and determine whether an inlet gas temperature exceeds a second temperature threshold to set a second chamber outlet set point.

Additionally or alternatively, the system in step 612 may determine whether the inlet temperature passes a different humidity metric. For example, the system may utilize a functional relationship between heat and humidity of the inlet gas in order to determine whether to reduce the maximum chamber outlet set point in step 616, 626, or 628 or continue with normal control in step 614 or 630. The functional relationship may take into account factors other than the current inlet temperature. This pressure value can be used to cap a maximum chamber outlet temperature and/or define a chamber outlet temperature if the pressure reading of the ambient air either exceeds a threshold or is below a threshold or is within a threshold range.

The threshold in step 612 may include a pre-determined temperature threshold or set of temperature thresholds. Pre-determined means the temperature threshold is pre-programmed into the controller. In an alternative form, the temperature threshold may not be pre-determined, but instead may be dynamically calculated based on one or more of an chamber outlet set point, heater plate temperature set point, a flow rate or target humidity. The temperature threshold may be calculated by the controller based on other factors e.g. patient end temperature set point or a desired (i.e. selected) patient end dew point. The temperature threshold may correspond to any number of temperatures. For example, the temperature threshold may be between 19° C. and 26° C. Throughout the disclosure, a temperature range that is between a first temperature and a second temperature includes both the first temperature and the second temperature. For example, the threshold temperature may preferably be between 22° C. and 24° C. The predetermined temperature threshold(s) may vary according to outlet temperature set point(s) of the humidifier. The predetermined temperature threshold(s) may also vary according to a target humidity value of the gas after it passes through the humidification chamber. A target humidity may be different for different modes of the humidifier. For example, the humidifier may have different modes of operation that deliver different temperature and humidity conditions of the gas to the patient based on therapeutic need, such as an invasive or non-invasive mode. Each operative mode may optionally include multiple desired dew points for delivery to the patient or modes. For example, a non-invasive mode (i.e. corresponding to non invasive ventilation delivery) may include a 27° C. desired dew point mode, a 29° C. mode, and a 31° C. mode, or other temperature modes. Each desired dew point or mode may correspond to a target humidity of the gas. Each desired dew point may have a corresponding shared or unique temperature threshold. For example, the 27° C. mode may have a corresponding temperature threshold of 22° C. The 29° C. and 31° C. modes may both have a corresponding temperature threshold of 24° C. Additionally or alternatively to the desired dew point modes, the operative modes may optionally include multiple chamber outlet set points.

Table 1 shows some example relevant ranges for maximum allowable chamber outlet temperature set points and corresponding chamber inlet temperature thresholds for a non-invasive therapy mode. As seen in the table the humidity level is defined both as mg/L as well as a dew point temperature. The dew point temperature can correspond to the required temperature of gases at the chamber outlet. "Chamber Inlet Threshold" refers to the chamber inlet temperature that indicates to the controller when to reduce the desired humidity level that is outputted by the humidifier and introduced to the incoming gases to a lower humidity level. "Dry humidity level range when chamber inlet is below the threshold" refers to the desired humidity level that the humidifier delivers when the inlet gas temperature is below the chamber inlet temperature threshold. This can correspond to what the humidifier does during normal operating conditions in the step 614 of FIG. 6A or under step 630 of FIG. 6B if the gas inlet temperature does not exceed the threshold temperature in decision block 612. "Dry humidity level range when chamber inlet is above the threshold" refers to the lowered humidity level that the humidifier delivers when chamber inlet temperature is exceeded. The ranges can correspond to the minimum allowable tolerance about the humidity level.

TABLE 1

Relevant parameters for first humidity level and second humidity level when temperature exceeds a threshold.

| | 31° C. Mode | 29° C. Mode | 27° C. Mode |
|---|---|---|---|
| Chamber Inlet temperature threshold | 24° C. | 24° C. | 22° C. |
| Dry humidity level range when chamber inlet is below the threshold | 31-33 mg/L equivalent to 30.7-31.9° C. dew point | 24-26 mg/L equivalent to 26.3-27.7° C. dew point | 22-23 mg/L equivalent to 24.8-25.6° C. dew point |
| Dry humidity level range when chamber inlet is above the threshold | 22-25 mg/L equivalent to 25-27° C. dew point | 15.3-27 mg/L equivalent to 19-25° C. dew point | 15.3-19.7 mg/L equivalent to 19-23° C. dew point |

In other examples, there may be other ranges for allowable chamber outlet temperature set points for other therapy modes. For example, in an invasive therapy mode (which corresponds to invasive ventilation therapy), a dry humidity level range when chamber inlet temperature is above the threshold can include 36-40 mg/L, which may be equivalent to 33-35° C. dew point for a 37° C. mode. In another example, in a high-flow mode (which corresponds to delivery of humidified high flow therapy), a dry humidity level range when chamber inlet temperature is above the threshold can include 36-40 mg/L, which may be equivalent to 33-35° C. dew point for a 37° C. mode, the threshold can include 26-34 mg/L, which may be equivalent to 28° C. dew point for a 35° C. mode, and/or the threshold can include 22-20 mg/L, which may be equivalent to 26° C. dew point for a 33° C. mode.

The system may control an amount of power provided to a heater in the humidifier to achieve a chamber outlet temperature set point. The heater may be a heater plate in the humidifier. For example, the system may control the amount of power to a heater plate to achieve that chamber outlet set point. The system may use a closed loop system, using feedback from the actual measured temperature at the chamber outlet to control the amount of power to the heater plate. The error value between measured chamber outlet temperature and chamber outlet set point may be used to either increase or reduce power provided to the heater plate. The system may control power by controlling a PWM module that supplies voltage to the power. The system may reduce the amount of power provided to a heater. For example, the system may set a power threshold or limit. The power threshold or limit may correspond to a dew point and/or a target humidity of the gas. For example, the power threshold may correspond to a dew point of 19° C. In another example, the power threshold may correspond to a humidity output of 15.3 mg/L. Additionally or alternatively, the system may reduce the amount of power by limiting the power according to a function or set of functions. For example, the system may cause the heater to output an amount of power according to a first function when the inlet temperature passes or does not pass a threshold temperature and cause the heater to output an amount of power according to a second function when the inlet temperature passes or does not pass a second threshold temperature. The first function may operate to control the amount of power to the heater plate, wherein the power may be capped by a maximum allowable power when the temperature (i.e. inlet temperature of gases) is below a threshold. The maximum allowable power may correspond to a safety limit for power provided to the heater plate. The second function may cap the maximum allowable heater plate power for a given inlet temperature when the inlet temperature of gases exceeds the threshold. That is, the second function may operate to control the amount of power to the heater plate, wherein the power is further limited below the maximum allowable power to the heater plate when the inlet temperature exceeds the threshold. The first and second function may correspond to any number of functions. In the second function the controller is configured to define a second maximum allowable power to the heater plate. The second maximum allowable power defines a new limit. The second maximum allowable power to the heater plate may be less than the maximum allowable power defined by the first function (i.e. a first maximum allowable heater plate power). The second maximum allowable power to the heater plate is a reduced value. The second maximum allowable power may correspond to a maximum allowable chamber outlet set point when the inlet temperature of gases exceeds the temperature threshold. The lower second allowable heater plate power provides a cap for the output humidity of the humidifier. This cap reduces the chances or over humidifying gases and helps to account for humidity in the gases due to air entraining gases sources e.g. air entraining ventilators. The maximum allowable heater plate power may be defined by a piece wise function. The piece wise function may be similar to or at least correspond to the piece wise function that defines the maximum allowable chamber outlet temperature set point. For example, the first and second function may together or separately operate as a piecewise function.

Figure 7:
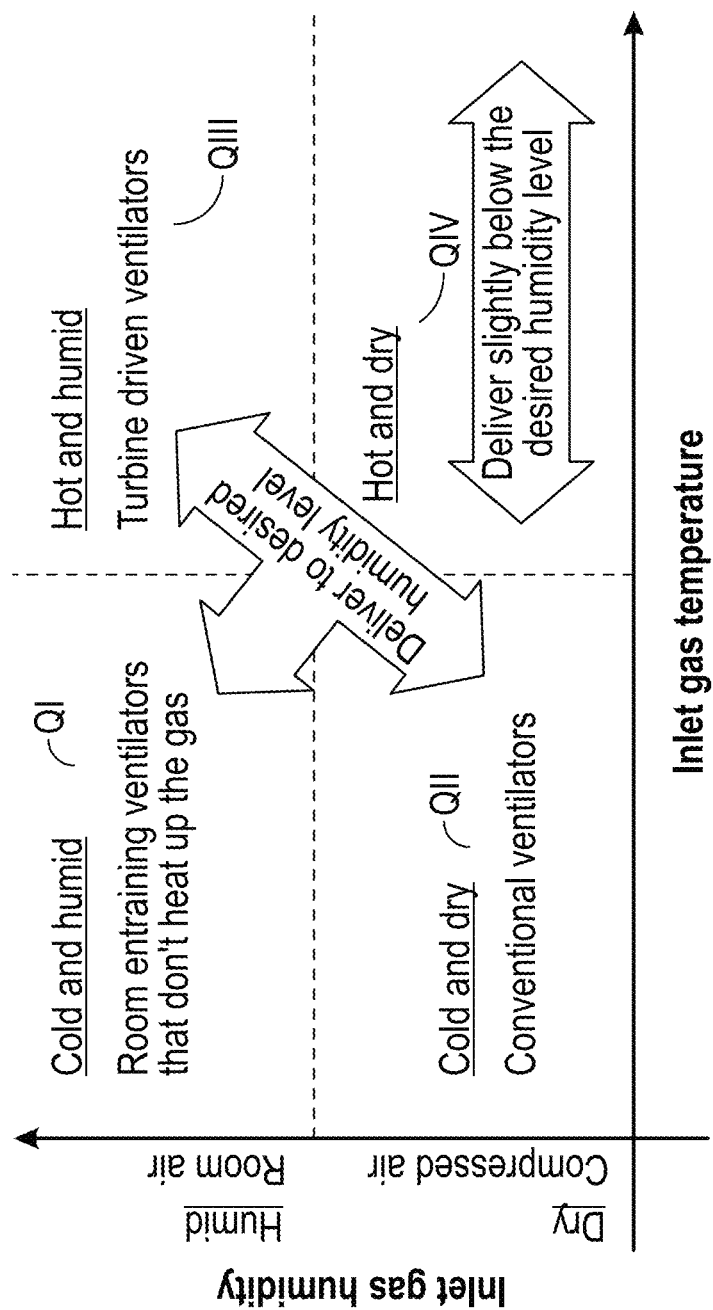
FIG. 7 illustrates example improved outlet humidity levels with respect to gas conditions at an inlet of a humidifier.

FIG. 7 illustrates example improved outlet humidity levels with respect to gas conditions at an inlet of a humidification chamber. As mentioned with regards to FIG. 3, without knowledge of the inlet humidity conditions, a humidifier can deliver close to desired humidity level in three out of four types of gas conditions: cold and humid (QI), cold and dry (QII), and hot and dry (QIV). However, there may be excess rain out in the inspiratory tube and/or patient interface at least in cases of incoming gases being hot and humid (QIII). Using the processes 600 and 601 shown in FIGS. 6A and 6B, a system can additionally effectively deliver a desired humidity level to quadrants I, II, and III, and a therapeutic humidity level to quadrant IV even when used with turbine driven ventilators or room entrained gas. A hot and dry inlet gas condition is less common because a hot inlet gas condition is usually associated with room air entraining ventilators which have turbines that generate heat. Therefore, the gas usually can have a humidity level significantly higher relative to 'dry' compressed bottle or wall gas. In this less common case of a hot and dry inlet gas condition, the delivered humidity level can reduce while still delivering a therapeutic level of humidity to the patient.

Figure 8:
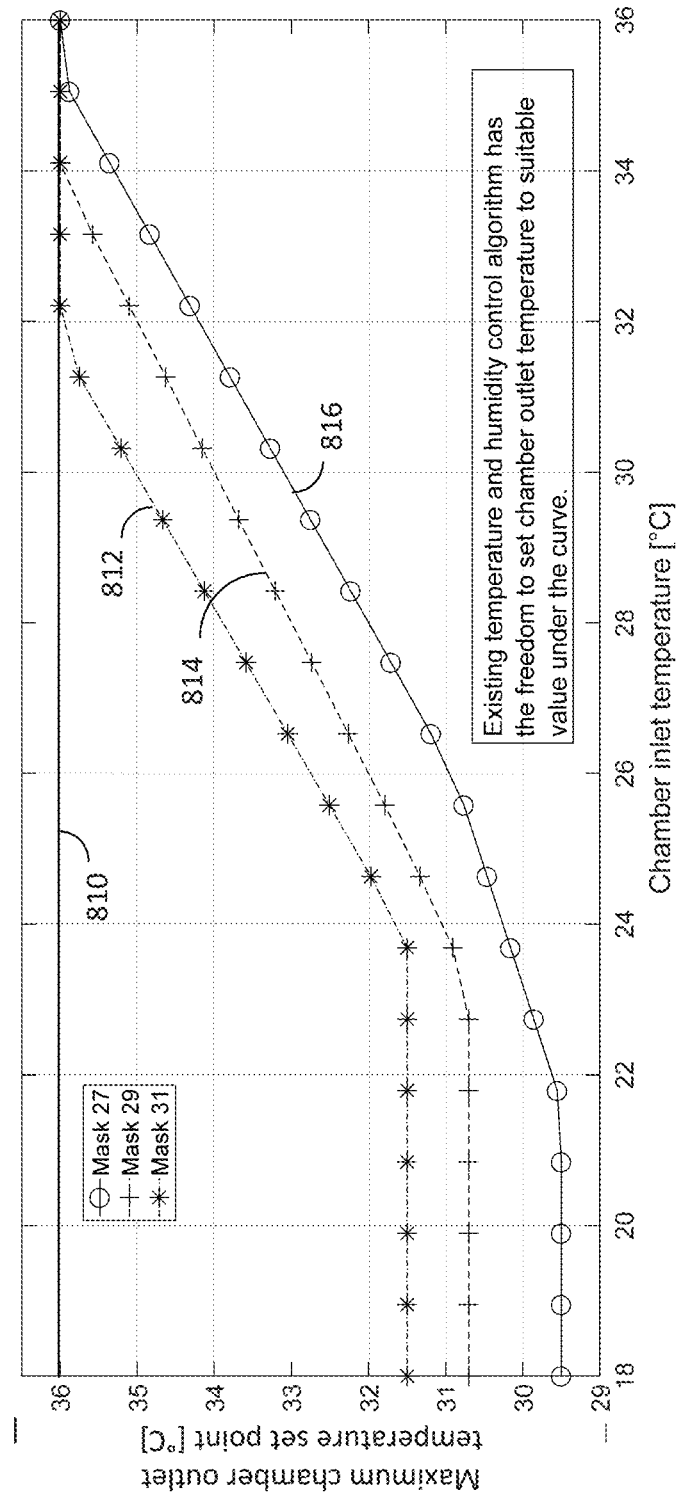
FIG. 8 illustrates example maximum chamber outlet temperature limits as a function of chamber inlet temperature at different example user settings for a humidifier.

FIG. 8 illustrates example maximum chamber outlet temperature set points as a function of chamber inlet temperature at different example outlet set points or user modes (illustrated as the Mask 27, Mask 29, and Mask 31 modes) for a humidifier operating as part of a non-invasive respiratory assistance system. The humidifier is operating in a non invasive mode. The non invasive mode may be selected by a graphical user interface e.g. a touchscreen located on the humidifier base unit. The system may modify the existing temperature and humidity control algorithm, such as in the step 616 of FIG. 6A, to set chamber outlet temperature set points to suitable values under the curve shown in FIG. 8 based on temperature thresholds for each outlet set point or user mode. The line 810 represents a first mode/function where the chamber outlet temperature set point is unbounded and the only limit is a high temperature limit (or temperature safety limit) and a first operation of the system when the inlet temperature is below a threshold temperature. In the first mode (i.e. first function) defines a maximum allowable chamber outlet temperature set point as 36° C., as defined by line 810. As seen in FIG. 8, the actual chamber outlet temperature set point used to control the power to the heater plate corresponds to the selected dew point i.e. 27° C. or 29° C. or 31° C., as per lines 812, 814, 816. These chamber outlet set points can vary depending on gases conditions such as for example flow rate, but these chamber outlet temperature set points will not exceed the maximum allowable limit defined by line 810 when in the first mode (i.e. when the inlet temperature is less than the temperature threshold). The line 810 may correspond to a temperature safety limit. Under the first mode/function, the system may set the chamber outlet temperature set point, anywhere under the line 810, which may correspond to a temperature below, for example, 36° C., which may operate as the temperature safety limit. In other words, under the first mode/function, which may occur at inlet temperatures below a threshold temperature, the system may cap the maximum chamber outlet temperature set point to a predetermined value and the system may adjust the chamber outlet temperature set point to any value up to 36° C. to achieve the desired humidity. Lines 812, 814 and 816 represent a second mode/function where the chamber outlet temperature set point is capped and may not exceed the maximum chamber outlet temperature set points along each line and a second operation of the system when the inlet temperature exceeds a threshold temperature. The chamber outlet temperature set point is set below the line of the curves of lines 812, 814 and 816 if the inlet temperature exceeds the threshold. Each line 812, 814, and 816 may correspond to a temperature differential between the inlet temperature and chamber outlet temperature. The differential may be sufficient to achieve a desired therapeutic humidity value (as per Table 1). The lines 812, 814, 816 define a maximum allowable chamber outlet temperature set point for the second mode or second function (i.e. when the inlet temperature of gases exceeds the temperature threshold). The lines 812, 814, 816 illustrate the chamber outlet set point in both the first mode and second mode. In the second mode i.e. when the inlet temperature exceeds the temperature threshold, the lines 812, 814, 816 define a maximum allowable chamber outlet temperature set point. This maximum allowable set point is less than the first maximum allowable set point for the first mode (i.e. when the inlet temperature is less than the temperature threshold), as defined by line 810. The line 810 in conjunction with any one of lines 812, 814, 816 express a piecewise function that defines the maximum allowable chamber outlet temperature set point. In the first mode i.e. first part of the piecewise function the maximum allowable set point is defined by line 810. The second part of the piecewise function the maximum allowable set point is defined by the line 812 or 814 or 816 respectively (depending on the selected dew point by the user). As also seen in FIG. 8, in the second mode the maximum allowable chamber outlet temperature set point reaches and stays at 36° C. when the inlet temperature exceeds a second temperature threshold. The second temperature threshold corresponds to an inlet temperature that exceeds the minimum temperature differential required. The second temperature threshold may be a single temperature value or a range of temperature values. Each mode e.g. 27, 29 or 31 degree mode may have its own second temperature threshold value. As seen in FIG. 8, the controller tries to maintain a temperature differential between the chamber outlet set point and the inlet temperature of gases. This temperature differential is used to define the chamber outlet temperature set point. The temperature differential is dependent on at least the flow rate and may also additionally be dependent on ambient temperature and heater plate temperature. As the inlet temperature of gases exceeds a second temperature threshold, the chamber outlet temperature set point is set to the maximum allowable chamber outlet set point of 36° C. as shown in FIG. 8. As shown in FIG. 8 the lines 812, 814 and 816 flatten out at 36° C. when the temperature differential between the inlet temperature and the chamber outlet set point is less than a differential threshold.

Figure 9A:
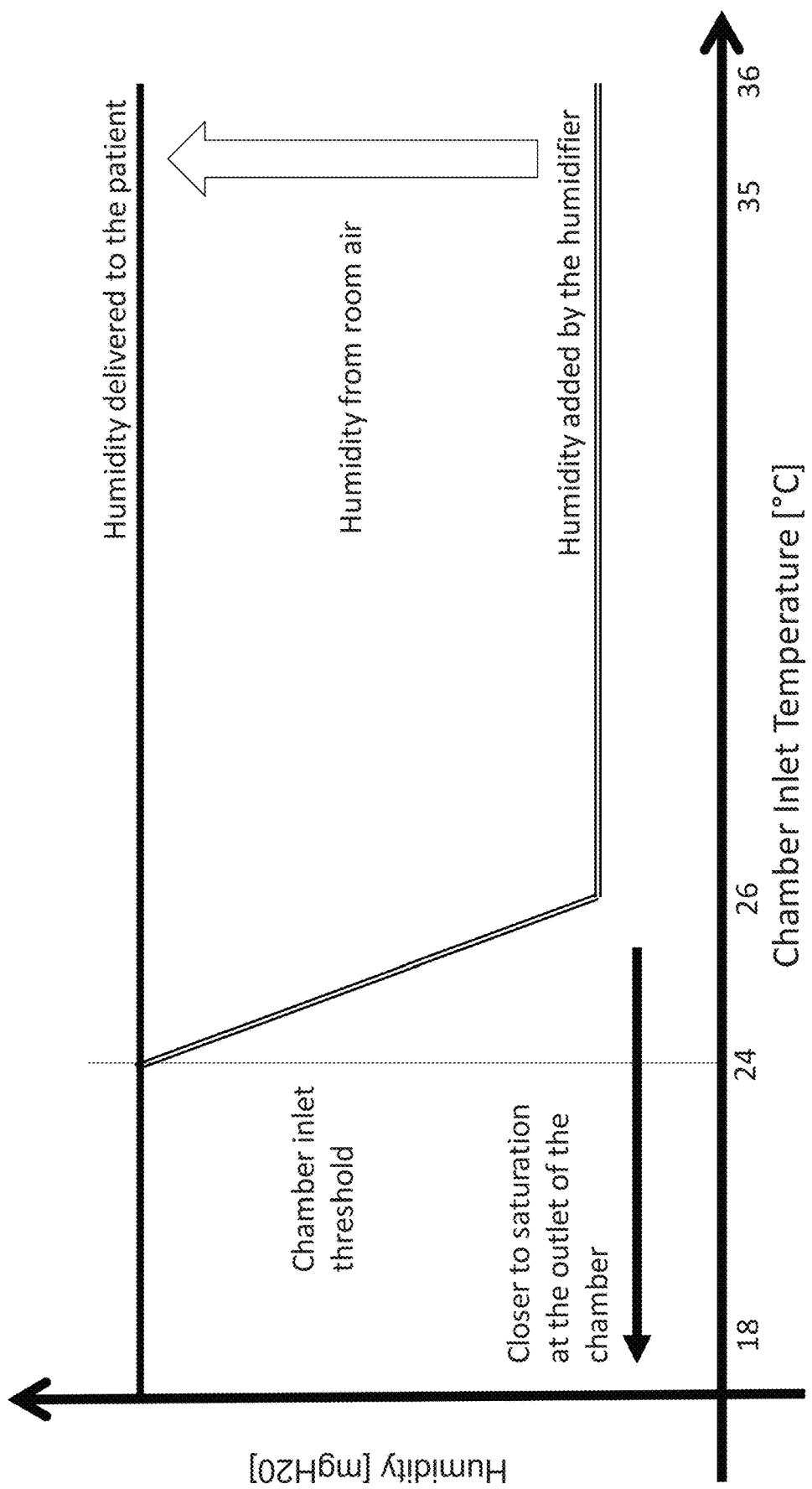
FIG. 9A illustrates an example of humidity added by an example humidifier as a function of inlet temperature and humidity added by the humidifier.

FIG. 9A illustrates an example of humidity added by an example humidifier as a function of inlet temperature and humidity added when inlet gas is dry. For example, when the chamber inlet temperature is low (for example, being less than a 24° C. threshold) the humidifier can deliver a desired humidity level to the incoming gases under normal operating conditions (for example, as shown in step 614 of FIG. 6A and under step 630 of FIG. 6B if the gas inlet temperature does not exceed the threshold temperature in decision block 612). When chamber inlet temperature increases above about 24° C., the system can reduce the humidity level (for example, as shown in step 616 in FIG. 6A and under step 630 of FIG. 6B if the gas inlet temperature exceeds the threshold temperature in decision block 612 and the system performs steps 626 and 628) to a lower desired humidity level to the incoming gases. As discussed above, when this algorithm is used with dry gas but of the same inlet temperature, which exceeds the temperature threshold (that is, hot and dry gases as shown in FIG. 7), the humidity level delivered to the patient is at a lower but therapeutic level. If the algorithm is used with a room air entraining ventilator (that is, producing hot and humid gases as shown in FIG. 7), the delivered humidity level to the patient or user is the lower desired humidity level plus the humidity from the room air. In other words, this lowered humidity level can account for room entrained humidity and minimize the problem illustrated in FIGS. 4A-4B and 5A-5B where the unaccounted for room air humidity increases the dew point to an undesirable higher level, leading to condensation (such as excess condensation that causes patient discomfort and/or disruption of the therapy to clean the patient interface and/or the inspiratory tube). Put another way, as shown in FIG. 9A, when the inlet temperature threshold is exceeded, the controller may control the heater plate to generate a lower absolute humidity in order to account for the increased amount of humidity from the ambient air. The lowered absolute humidity value and the humidity from the incoming air may result in an absolute humidity that is at or above a therapeutic value and reduces or minimizes condensation in the tube or patient interface.

Figure 9B:
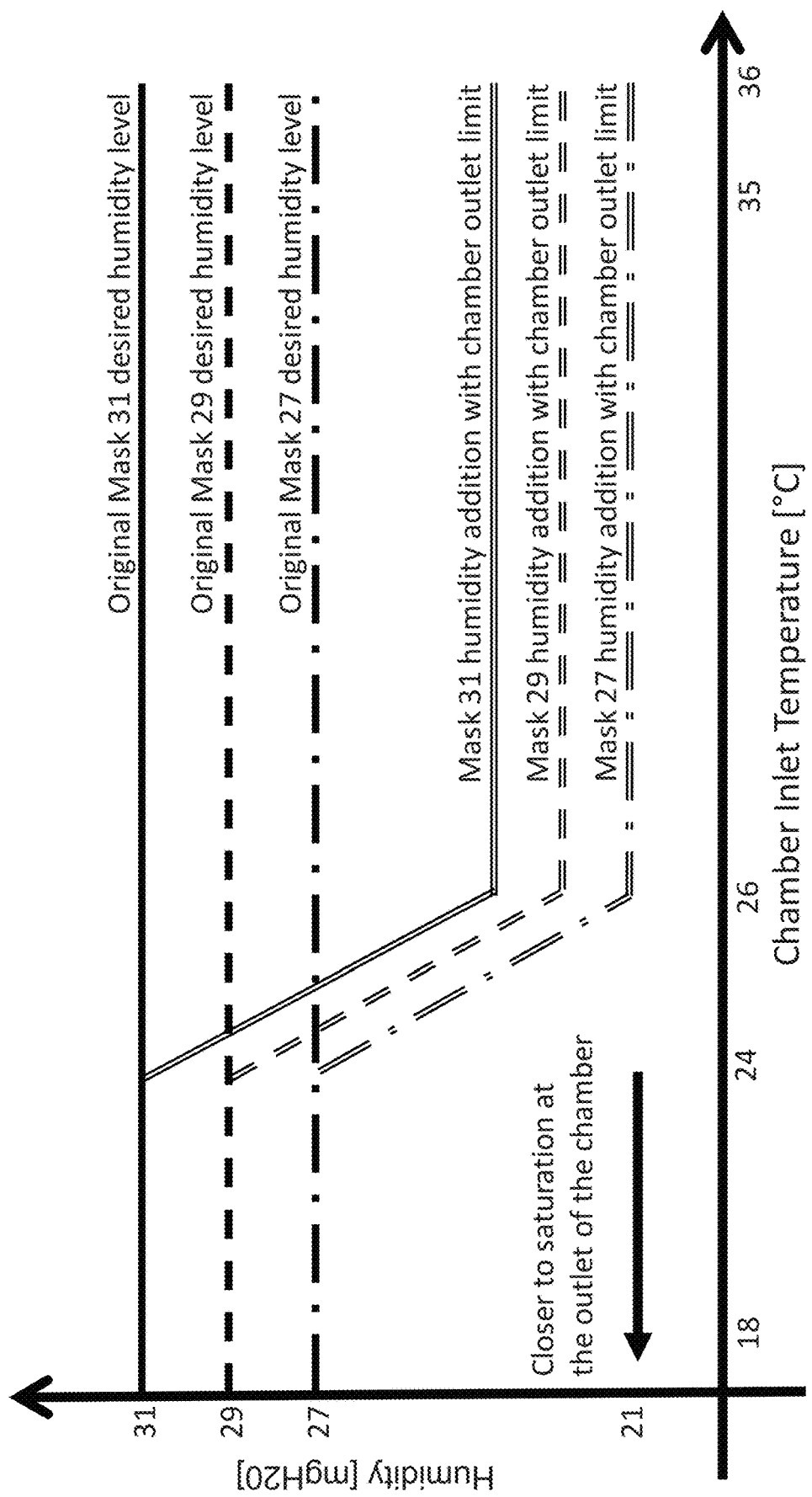
FIG. 9B illustrates an example of humidity added by an example humidifier as a function of inlet temperature and humidity added by the humidifier.

FIG. 9B illustrates an example of humidity added by an example humidifier as a function of inlet temperature and humidity added when inlet gas is dry for different example user settings or outlet temperature set points. In particular, FIG. 9B illustrates the effects of lowered humidity levels for a non-invasive mode of operation of a humidifier with different user settings or chamber outlet temperature set points of 27° C., 29° C., and 31° C., corresponding to Mask 27, Mask 29, and Mask 31 respectively. Additionally or alternatively, the maximum chamber outlet temperature set point(s) may be set at a reduced level to minimize condensation (for example, 25° C., 27° C., 29° C. corresponding to Mask 27, Mask 29, and Mask 31 respectively). For high flow mode a similar approach may be adopted by the controller. Alternatively in high flow mode there may be no changes to the maximum allowable humidity. During invasive mode the humidity is maximized and unchanged across all inlet temperature ranges.

Example Humidity Delivery Control Systems

Figure 10A:
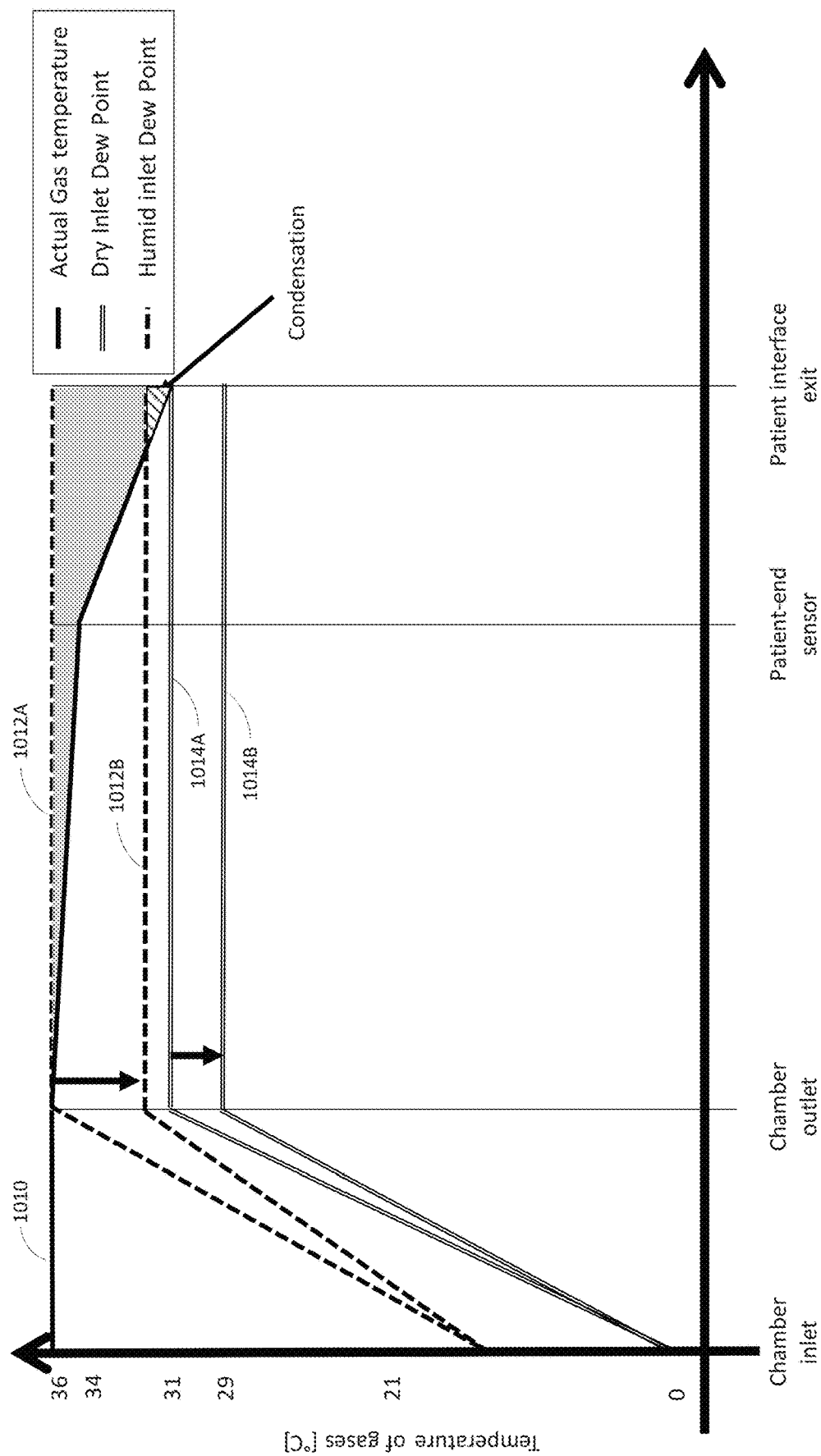
FIG. 10A is a graph showing an example operation of an example humidity delivery control system in a non-invasive mode at an inlet temperature of 36° C.
Figure 10B:
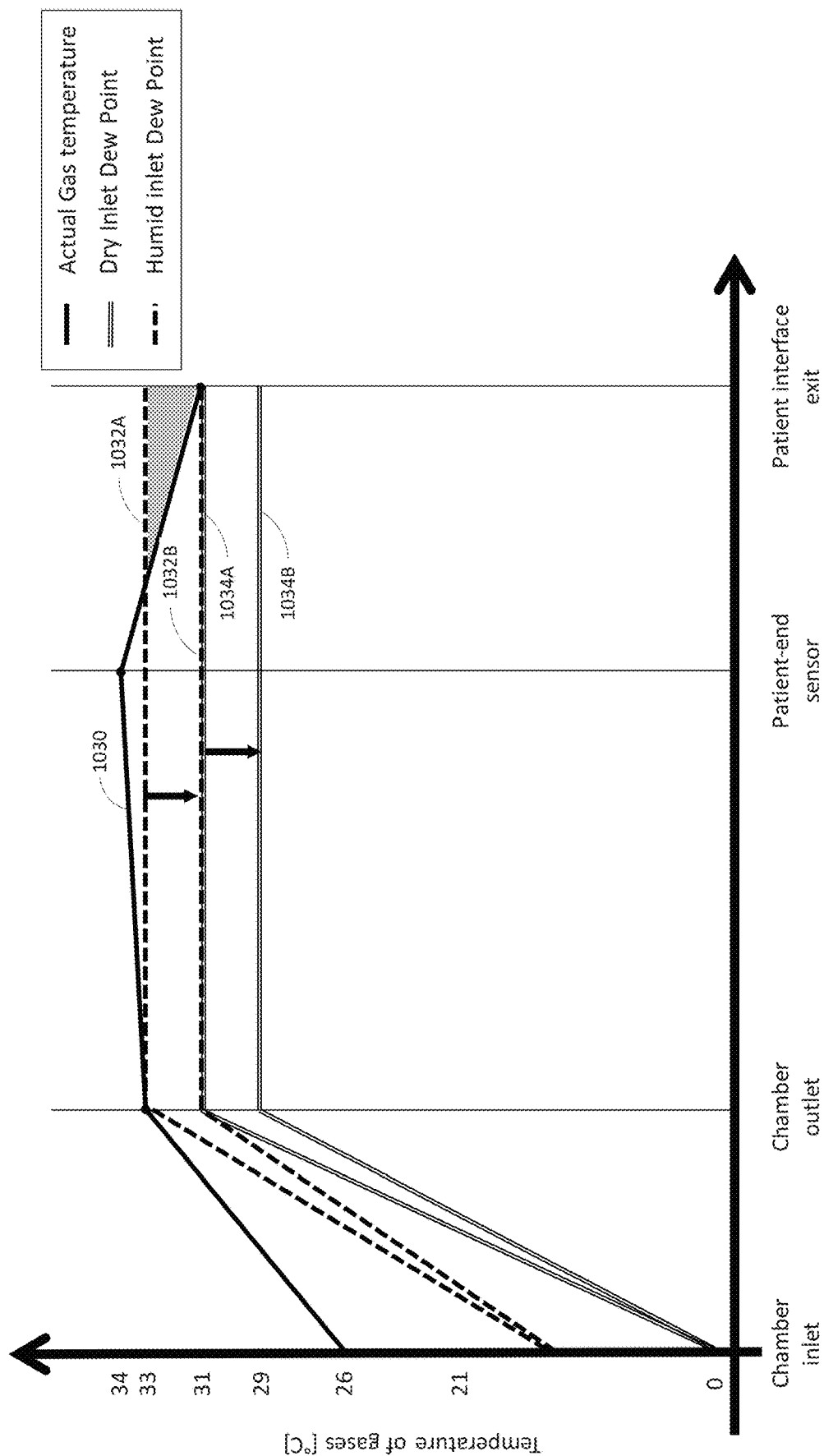
FIG. 10B is a graph showing an example operation of an example humidity delivery control system in a non-invasive mode at an inlet temperature of 26° C.
Figure 10C:
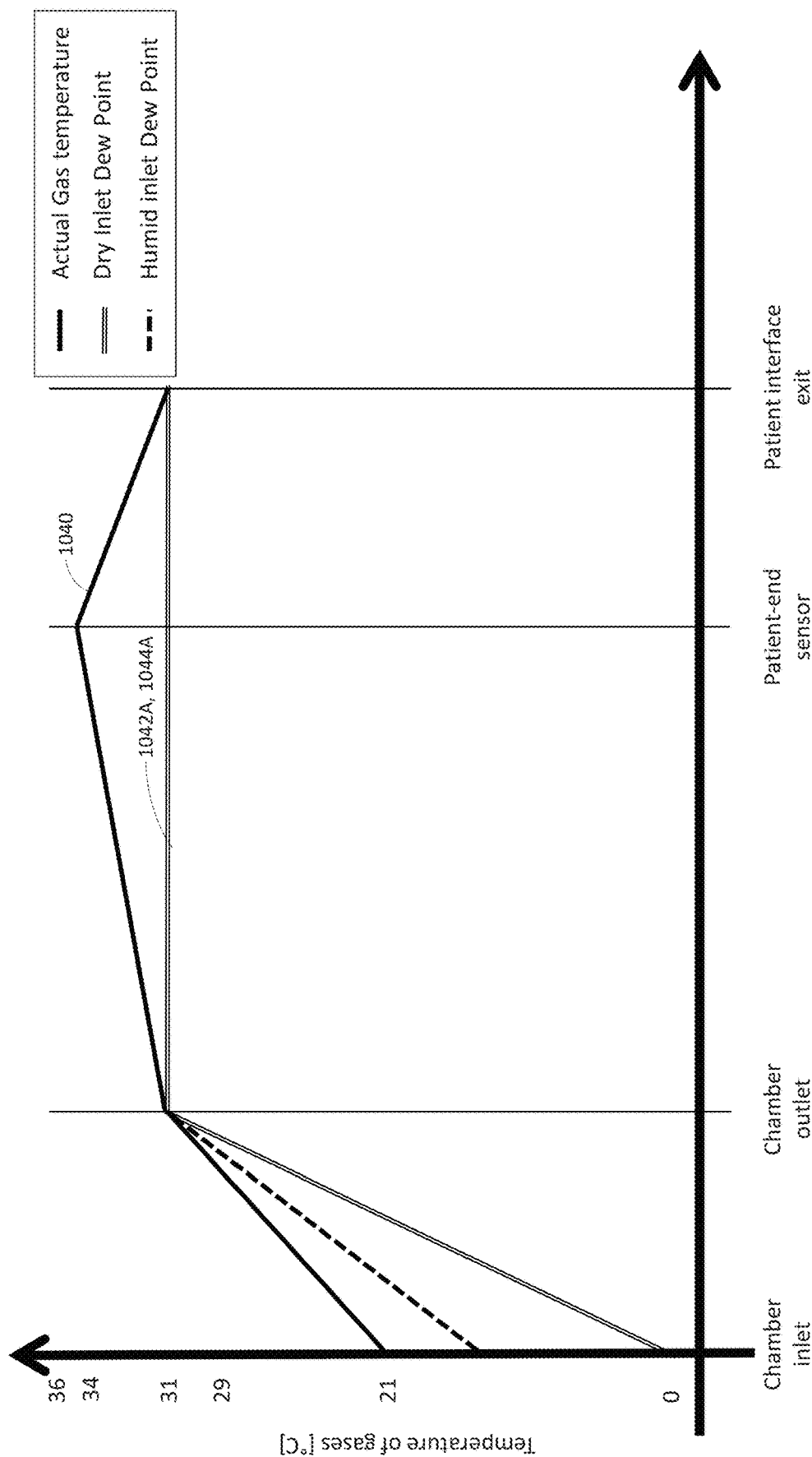
FIG. 10C is a graph showing an example operation of an example humidity delivery control system in a non-invasive mode at an inlet temperature of 21° C.

FIGS. 10A-10C illustrates an example superimposition of FIGS. 5A-C with a proposed solution to condensation that may form under normal operation as illustrated in FIGS. 5A-5C.

FIG. 10A is a graph showing an example effect of an example humidity delivery control system at an inlet temperature of 36° C. In particular, FIG. 10A shows the comparison of operating a humidifier under normal operating conditions with a target or desired humidity corresponding to a 31° C. dew point (such as shown in FIG. 5A) and operating the humidifier with a reduced maximum chamber outlet set point corresponding to a 29° C. dew point. An example actual gas temperature as it passes through a humidifier is shown by line 1010. The gas temperature may decrease from an outlet temperature, shown as 36° C. in FIG. 10A, to a target temperature at the patient interface exit, for example, shown as 31° C. in FIG. 10A. When the gas is room entrained, it may contain excess humidity. When the gas is not room entrained, it may be considered "dry." Under the process 601 shown in 6A or the process 600 shown in FIG. 6B, a target or desired humidity level, represented by dry inlet humidity (i.e. dry gases) (line 1014A), may be shifted down to a lower desired humidity level corresponding to, for example, a 29° C. dew point (line 1014B). Line 1014A may represent a dew point when the system does not cap the chamber outlet set point if the inlet gases temp threshold is not exceeded. Line 1014B may represent the dew point resulting from lowering the chamber outlet set point once a temperature threshold is exceeded. For room entrained gas, the effective target humidity of the outlet gas may be lowered from line 1012A to line 1012B. Line 1012A may represent the dew point of the chamber humidity plus the ambient gases humidity (as shown in FIG. 5A). Line 1012B may represent the dew point of the chamber humidity plus the ambient gases humidity resulting once a temperature threshold is exceeded and a chamber outlet temperature set point is lowered (i.e. the maximum allowable chamber outlet temperature set point is capped). The lines 1012B and 1014B may represent a dew point change due to the lowered chamber outlet set point due, for example, to capping a chamber outlet temperature set point. Lines 1012B and 1014B may represent a dew point reduction because there is a reduced amount of humidity added to the gases by the humidifier when the chamber outlet set point is reduced. When the inlet temperature threshold is exceeded, the controller may cap the chamber outlet temperature set point (or a heater plate power set point or a heater plate temperature set point or a humidity set point) to a lower chamber outlet set point (or lower heater plate power set point or a heater plate temperature set point or lower humidity set point) as compared to the normal control (represented by line 1014A). Additionally or alternatively to capping a chamber outlet temperature set point, a heater plate set point temperature may be capped or the heater plate power set point may be capped. The lower chamber outlet temperature set point may result in a lower dew point and less absolute humidity output by the humidifier. Less condensation, shown by the hatched triangle, may be formed when the humidifier is connected with a room air entraining ventilator because the dew point is lowered from 1012A to 1012B. This is achieved by capping the chamber outlet temperature set point (or capping the heater plate power set point or heater plate temperature set point) to produce less humidity. The capped chamber outlet temperature set point (or capped heater plate power set point or heater plate temperature set point) correspond to a maximum allowable set point. The capped set point in the second mode (i.e. when the inlet temperature is equal to or exceeds a temperature threshold) is lower than the maximum set point of a first mode (i.e. when the inlet temperature is less than the temperature threshold). While there may still be some condensation that occurs because the inlet temperature is high, the condensation in FIG. 10A may be significantly lowered as compared to a condensation level for gases during a normal operation of the humidifier, as shown in FIG. 5A. As noted above, Lines 1012A, 1012B, 1014A, and 1014B are shown as straight horizontal lines representing extrapolated dew points for explanatory purposes to show a point or points at which condensation may occur in the humidifier or respiratory assistance system.

FIG. 10B is a graph showing an example effect of an example humidity delivery control system at an inlet temperature of 26° C. In particular, FIG. 10B shows an example comparison of operating a humidifier under normal operating conditions with a target humidity corresponding to a 31° C. dew point (such as shown in FIG. 5B) and operating the humidifier with a reduced maximum chamber outlet set point corresponding to a 29° C. dew point. An example gas temperature as it passes through a humidifier is shown by line 1030. Under the process 600, a target humidity level, represented by dry inlet humidity (line 1034A), may be shifted down to a lower desired humidity level corresponding to, for example, a 29° C. (line 1034B) dew point. Line 1034A may represent a dew point at the chamber outlet when the system does not further cap the chamber outlet temperature set point, if the inlet gases temperature threshold is exceeded. Line 1034B may represent the dew point at the chamber outlet resulting from lowering (i.e. capping) the chamber outlet temperature set point, once a temperature threshold is exceeded. The chamber outlet temperature set point is capped to maximum allowable chamber outlet temperature set point For room entrained gas, the effective target humidity of the outlet gas may be lowered from line 1032A to line 1032B. Line 1032A may represent the dew point at the chamber outlet (as shown in FIG. 5B). An outlet temperature of the gases may be 33° C. Because this outlet temperature is lower than the chamber outlet temperature setpoint and/or the temperature that is desired at the patient end, which is 34° C. in this example, the system will be configured to heat the gases as the gases travel from the chamber outlet to the patient end, shown by line 1030 between the chamber outlet and patient-end sensor. The gases will then cool down as the gases travel through patient interface which is unheated to about 31° C. at the patient-interface exit, shown by line 1030 between the patient-end sensor and patient interface exit. As the gases cool down between the patient end and the patient-interface exit, the dew point of the gases will also decrease. As mentioned above, the water vapor that can no longer be contained in the gases with the lower dew point of 31° C. will condense into a liquid. This condensation is represented by the grey area in FIG. 10B. Line 1032B may represent the dew point at the chamber outlet resulting once an inlet temperature threshold is exceeded and a chamber outlet set point is lowered. The lines 1032B and 1034B may represent a dew point change due to the lowered chamber outlet set point due, for example, to capping a chamber outlet set point. Lines 1032B and 1034B may represent a dew point reduction because there is a reduced amount of humidity added to the gases by the humidifier when the chamber outlet set point is reduced (i.e. maximum allowable chamber outlet set point is capped). When the inlet temperature threshold is exceeded, the controller may cap the chamber outlet set point (or a heater plate power set point or a heater plate temperature set point) to a lower chamber outlet set point as compared to the normal control (represented by line 1034A). Additionally or alternatively to capping a chamber outlet set point, a heater plate set point temperature may be capped or the heater plate power set point may be capped. The lower chamber outlet set point may result in a lower dew point and less absolute humidity. The lower i.e. capped chamber outlet set point corresponds to a maximum allowable chamber set point in the second mode (i.e. when the inlet gases temperature exceeds the temperature threshold). The maximum allowable chamber set point may change relative to changes in the inlet gases temperature. Condensation, such as represented by the shaded area, may be avoided by lowering the desired humidity dew point, also referred to as the actual dew point. For example reducing condensation can be achieved by capping the chamber outlet temperature set point (or capping the heater plate temperature set point or the heater plate power set point) if the inlet gases temperature exceeds a temperature threshold. As noted above, Lines 1032A, 1032B, 1034A, and 1034B are shown as straight horizontal lines representing extrapolated dew points for explanatory purposes to show a point or points at which condensation may occur in the humidifier or respiratory assistance system.

FIG. 10C is a graph showing an example effect of an example humidity delivery control system at an inlet temperature of 21° C., which is below a threshold temperature of 24° C. An example gas temperature as it passes through a humidifier is shown by line 1040. The target humidity dew point may remain at a line 1042A rather than being lowered because the inlet temperature threshold has not been exceeded. In the example shown in FIG. 10C, the humidifier can heat and humidify the gases to saturation at the lowered humidity level regardless of inlet humidity due to the low inlet temperature (that is, lower than the ambient temperature). This is shown by the merging of the dry inlet and humid inlet humidity lines (that is, line 1042A and 1044A are the same after the gas exits the chamber outlet). Lines 1042A and 1044A are shown as straight horizontal lines representing extrapolated dew points for explanatory purposes to show a point or points at which condensation may occur in the humidifier or respiratory assistance system.

In an alternative configuration the humidifier may comprise a humidity sensor at the outlet of the humidifier instead of a temperature sensor. The controller is configured to control power supplied to the heater plate based on the measured inlet temperature. The controller may be configured to operate in a first mode when the inlet temperature of gases is less than a threshold temperature and a second mode when the inlet temperature of gases exceeds a temperature threshold. The controller is configured to define a first maximum allowable humidity value in the first mode and a second maximum allowable humidity in the second mode. The second allowable humidity is less than the first maximum allowable humidity. The controller determines a humidity of gases based on the outlet humidity sensor. The controller is configured to control the power to the heater plate based to achieve a desired humidity output at the chamber outlet. In the second mode the heater plate power level is controlled to ensure the output humidity at the chamber outlet is less than the second maximum allowable humidity. The humidity set point may be defined by a piecewise function. The first portion of the piece wise function defines the first maximum allowable humidity output when the inlet temperature of gases is less than the temperature threshold. The second part of the function defines the second humidity output. The humidity setpoint may be modulated by the controller based on at least the inlet temperature and flow readings, in the second mode. However the maximum allowable humidity corresponds to the second maximum allowable humidity. The humidity set point may be adjusted to be lower than the second maximum allowable humidity corresponding to the desired humidity input by the user. However, when in the second mode (i.e. the inlet temperature of gases exceeds the temperature threshold), the humidity output will not exceed the second maximum allowable humidity. If the humidity output exceeds the second maximum allowable humidity, the heater plate power would be switched off by the controller. The lower humidity when the inlet temperature exceeds a temperature threshold, reduces condensate within the tube and/or the patient interface. The lower humidity output helps to prevent over humidification of gases, especially gases received from air entraining ventilators. In a further alternative configuration the system can work in conjunction with a humidity sensor measuring the inlet gases to determine if the gases are hot and humid or hot and dry. The system may utilize this additional information to change or refine the outlet temperature set point. Additionally or alternatively, the system can work in conjunction with a pressure sensor measuring the inlet gases that is configured to determine the ambient air pressure. The ambient air pressure can be used to determine an indicative humidity of the inlet gases.

Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor comprising digital logic circuitry, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A humidification apparatus for humidifying a gases flow provided to a user, the humidification apparatus comprising:
   a base unit comprising a heater plate;
   a humidification chamber configured to retain a humidification fluid, the humidification chamber comprising:
      a conductive base,
      one or more wall portions configured to couple to the base unit,
      an inlet, and
      an outlet;
   at least one inlet temperature sensor located within or adjacent the inlet of the humidification chamber;
   at least one outlet temperature sensor located within or adjacent the outlet of the humidification chamber; and
   a controller configured to:
      output a heater plate control signal to control an amount of power provided to the heater plate based at least partly on a function of an outlet temperature measured from signals received from the at least one outlet temperature sensor;

determine an inlet temperature of gases being received into the humidification chamber based on signals received from the at least one inlet temperature sensor;

determine if the inlet temperature exceeds a threshold temperature; and reduce, in response to the inlet temperature exceeding the threshold temperature, a maximum target humidity, added by the humidification apparatus, of gases leaving the outlet of the humidification chamber, wherein the threshold temperature varies according to an outlet temperature set point.

2. The humidification apparatus of claim 1, wherein the controller is further configured to limit the amount of power provided to the heater plate in response to the inlet temperature exceeding the threshold temperature.

3. The humidification apparatus of claim 2, wherein the controller is configured to limit the amount of power to less than or equal to a power threshold.

4. The humidification apparatus of claim 3, wherein the power threshold is set to achieve a minimum dew point of 19° C.

5. The humidification apparatus of claim 4, wherein the power threshold is set to achieve a minimum humidity output of 15 mg/L.

6. The humidification apparatus of claim 1, wherein the controller is further configured to control or limit the amount of power provided to the heater plate according to a first mode when the inlet temperature is below the threshold temperature and a second mode when the inlet temperature exceeds the threshold temperature.

7. The humidification apparatus of claim 1, wherein the controller is further configured to limit the outlet temperature set point if the inlet temperature exceeds the threshold temperature to define a maximum allowable outlet temperature set point.

8. The humidification apparatus of claim 1, wherein the threshold temperature is between 22° C. and 24° C.

9. The humidification apparatus of claim 1, wherein a desired dew point is selectable by the user.

10. The humidification apparatus of claim 1, wherein the humidification apparatus is operable in one of a plurality of modes, each mode of the plurality of modes defining a plurality of outlet temperature set points, the controller further configured to limit the amount of humidity generated based on the inlet temperature exceeding the threshold temperature, when operating in any one of the plurality of modes.

11. The humidification apparatus of claim 10, wherein the plurality of modes comprises an invasive mode, a non-invasive mode, and a high flow mode.

12. The humidification apparatus of claim 11, where the controller is configured to limit the humidity added to incoming gases when operating in the non-invasive mode.

13. The humidification apparatus of claim 11, wherein the any one of the plurality of modes is manually selectable by the user.

14. The humidification apparatus of claim 11, wherein at least one mode of the plurality of modes comprises user-selectable dew points of 27° C., 29° C., and 31° C.

15. The humidification apparatus of claim 11, wherein at least one mode of the plurality of modes comprises user-selectable dew points of 31° C., 34° C., and 37° C.

16. The humidification apparatus of claim 10, wherein the maximum target humidity for each outlet temperature set point of the plurality of outlet temperature set points is predefined when the inlet temperature is below the threshold temperature and an amount of humidity generated for each outlet temperature set point is reduced to a lower predefined value if the inlet temperature exceeds the threshold temperature.

17. The humidification apparatus of claim 14, wherein the at least one mode comprises the non-invasive mode.

18. The humidification apparatus of claim 15, wherein the at least one mode comprises the non-invasive mode.

* * * * *